United States Patent
Hinton et al.

(10) Patent No.: US 7,217,798 B2
(45) Date of Patent: *May 15, 2007

(54) ALTERATION OF FC-FUSION PROTEIN SERUM HALF-LIVES BY MUTAGENESIS

(75) Inventors: Paul R. Hinton, Sunnyvale, CA (US); Naoya Tsurushita, Palo Alto, CA (US)

(73) Assignee: PDL BioPharma, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/966,673

(22) Filed: Oct. 15, 2004

(65) Prior Publication Data

US 2005/0226864 A1 Oct. 13, 2005

Related U.S. Application Data

(60) Provisional application No. 60/562,627, filed on Apr. 14, 2004, provisional application No. 60/511,687, filed on Oct. 15, 2003.

(51) Int. Cl.
- C12P 21/08 (2006.01)
- C12P 21/06 (2006.01)
- C12P 21/04 (2006.01)
- C07K 16/00 (2006.01)
- C12N 15/00 (2006.01)

(52) U.S. Cl. .............................. 530/387.3; 530/387.1; 530/388.1; 435/69.1; 435/69.6; 435/326; 435/440; 435/455

(58) Field of Classification Search ..................... None
See application file for complete search history.

(56) References Cited

U.S. PATENT DOCUMENTS

| | | | |
|---|---|---|---|
| 5,530,101 | A | 6/1996 | Queen et al. |
| 5,834,597 | A | 11/1998 | Tso et al. |
| 5,994,514 | A | 11/1999 | Jardieu et al. |
| 6,165,745 | A | 12/2000 | Ward et al. |
| 6,277,375 | B1 | 8/2001 | Ward |
| 6,329,511 | B1 | 12/2001 | Vasquez et al. |
| 6,528,624 | B1 | 3/2003 | Idusogie et al. |
| 6,797,493 | B2 * | 9/2004 | Sun et al. ............ 435/69.7 |
| 7,083,784 | B2 | 8/2006 | Dall'Acqua et al. |
| 2001/0033842 | A1 | 10/2001 | Jardieu et al. |
| 2002/0098193 | A1 | 7/2002 | Ward |
| 2003/0003098 | A1 | 1/2003 | Strom |
| 2003/0044858 | A1 | 3/2003 | Jardieu et al. |
| 2005/0014934 | A1 * | 1/2005 | Hinton et al. ............ 530/387.3 |
| 2005/0032114 | A1 * | 2/2005 | Hinton et al. ............ 435/7.1 |
| 2005/0226884 | A1 | 10/2005 | Hinton et al. |
| 2005/0278799 | A1 | 12/2005 | Hinton et al. |
| 2006/0198640 | A1 | 9/2006 | Dall'Acqua et al. |

FOREIGN PATENT DOCUMENTS

| | | |
|---|---|---|
| EP | 1260521 A2 | 11/2002 |
| WO | WO93/04173 A1 | 8/1991 |
| WO | WO98/31229 A1 | 4/1995 |
| WO | WO97/28267 A1 | 2/1996 |
| WO | WO97/34631 A1 | 3/1996 |
| WO | WO98/05787 A1 | 6/1996 |
| WO | WO98/47531 A1 | 4/1997 |
| WO | WO99/02709 A1 | 7/1997 |
| WO | WO97/34621 A1 | 9/1997 |
| WO | WO98/23289 A1 | 6/1998 |
| WO | WO00/42072 A2 | 1/1999 |
| WO | WO00/47625 A1 | 2/1999 |
| WO | WO99/51642 A2 | 10/1999 |
| WO | WO99/58572 A1 | 11/1999 |
| WO | WO01/58957 A1 | 2/2000 |
| WO | WO00/68381 A1 | 11/2000 |
| WO | WO02/060919 A2 | 8/2002 |
| WO | WO2004/092219 A2 | 10/2004 |

OTHER PUBLICATIONS

Ellison et al. PNAS. 1982, 79:1984-1988.*
Attwood, Science 2000; 290:1-5 (html format).*
Skolnick et al. Trends in Biotech. 2000; 18:(1):34-39.*
Martin et al. Molecular Cell, 2001, 7:867-877.*
Ghetie, Victor, et al. "Increasing the serum persistence of an IgG fragment by random mutagenesis", *Nature Biotechnology* (1997) 15(7):637-640.
Hinton, Paul R., et al. "Engineered Human IgG Antibodies with Longer Serum Half-lives in Primates", *The Journal of Biological Chemistry* (2004) 279(8):6213-6216.
Achatz, et al. "The IgE antigen Receptor: a Key Regulator for the Production of IgE Antibodies", *Int. Arch. Allergy Immunol*, (2001) 124(1-3):31-4.
Alegre, et al. "Effect of a single amino acid mutation on the activating and immunosuppressive properties of a humanized OKT3 monoclonal antibody", *J. Immunol.* (1992) 148(11):3461-8.
Angal, et al. "A single amino acid substitution abolishes the heterogeneity of chimeric mouse/human (IgG4) antibode", *Mol. Immunol* (1993) 30(1):105-8.
Armour, et al. "Recombinant human IgG molecules lacking Fcgamma receptor 1 binding and monoctye triggering activities", *Eur J. Immunol.* (1999) 29(8):2613-24.
Armour, et al. The Contrasting IgG-Binding Interactions of Human and Herpes Simplex Virus Fc Receptors, *Biochem Soc. Trans.* (2002) 30(4):495-500.
Arya, et al. "Mapping of amino acid residues in the C mu 3 domain of mouse IgM important in macromolecular assembly and complement-dependent cytolysis", *J. Immunol* (1994) 152(3):1206-12.

(Continued)

*Primary Examiner*—Phillip Gambel
*Assistant Examiner*—Chun Crowder
(74) *Attorney, Agent, or Firm*—Townsend and Townsend and Crew LLP

(57) ABSTRACT

The present invention provides for a modified Fc-fusion protein in which at least one amino acid from the heavy chain constant region selected from the group consisting of amino acid residues 250, 314, and 428 is substituted with another amino acid which is different from that present in the unmodified Fc-fusion protein, thereby altering the binding affinity for FcRn and/or the serum half-life in comparison to the unmodified Fc-fusion protein.

15 Claims, 4 Drawing Sheets

OTHER PUBLICATIONS

Batra, et al. "Insertion of Constant Region Domains of Human IgG1 into CD4-PE40 Increases Its Plasma Half-Life", *Molec. Immunol.* (1993) 30(4):379-386.

Brekke, et al. "Human IgG isotype-specific amino acid residues affecting complment-mediated cell lysis and phagocytosis", *Eur. J. Immunol.* (1994) 24(10):2542-7.

Burmeister, et al. Crystal structure of the complex of rat neonatal Fc receptor with Fc *Nature* (1994) 372:379-383.

Canfield "The binding affinity of human IgG for its high affinity Fc receptor is determined by multiple amino acids in the CH2 domain and is modulated by the hinge region", *J. Exp. Med.* (1991) 173(6):1483-91.

Caron, et al. "Engineered humanized dimeric forms of IgG are more effective antibodies", *J. Exp. Med.* (1992) 176(4): 1191-5.

Chapman, et al. "Characterization of the Interaction Between the Herpes Simplex Virus Type 1 Fc Receptor and Immunoglobulin G", *J. Biol. Chem.* (1999) 274(11):6911-9.

Chappel, et al. "Identification of a secondary Fc gamma R1 binding site within a genetically engineered human IgG antibody", *J. Biol. Chem.* (1993) 268(33): 25124-31.

Chaudhury, et al. "The Major Histocompatibility Complex-related Fc Receptor for IgG (FcRn) Binds Albumin and Prolongs Its Lifespan", *J. Exp. Med.* (2003) 197(3):315-322.

Chintalacharuvu, et al. "Hybrid IgA2/IgG1 Antibodies with Tailor-Made Effector Functions", *Clin. Imm.* (2001) 101(1):21-31.

Cole, et al. "HuM291, A Humanized Anti-CD3 Antibody, is Immunosuppressive to T cells While Exhibiting Reduced Mitogenicity in Vitro", *Transplantation* (1999) 68(4):563-71.

Cole, et al. "Human IgG2 variants of chimerical anti-CD3 are nonmitogenic to T cells", *J. Immunol.* (1997) 159(7): 3613-21.

Dall'acqua, et al. "Increasing the Affinity of a Human IgG1 for the Neonatal Fc Receptor: Biological Consequences", *J. Immunol.* (2002) 169(9):5171-80.

Deisenhofer "Crystallographic refinement and atomic models of a human Fc fragment and its complex with fragment B of protein A from *Staphylococcus aureus* at 2.9- and 2.8-A resolution", *Biochemistry* (1981) 20:2361-2370.

Delano, et al. "Convergent Solutions to Binding at a Protein-Protein Interface", *Science* (2000) 287(5456):1279-83.

Dorai, et al. "Role of inter-heavy and light chain disulfide bonds in the effector functions of human immunoglobulin IgG1", *Mol. Immunol.* (1992) 29(12):1487-91.

Duncan, et al. "The binding site for C1q on IgG", *Nature* (1988) 332(6166):738-40.

Ehrlich, et al. "Characterization of human monoclonal antibodies directed against hepatitis B surface antigen", *Hum. Antibodies Hybridomas* (1992) 3:2-7.

El-Amine, et al. "In Vivo Induction of Tolerance by an Ig Peptide is not Affected by the Deletion of FcR or a Mutated IgG Fc Fragment", *Int. Immunol.* (2002) 14(7):761-6.

Firan, et al. "The MHC Class I-Related Receptor FcRn, Plays an Essential Role in the Matermofetal Transfer of Gamma-Globulin in Humans", *Int. Immunol.* (2001) 13(8):993-1002.

Ghetie and Ward "Multiple roles for the major histocompatibility complex class I-related receptor FcRn", *Annu. Rev. Immunol.* (2000) 18:739-766.

He X-y, et al. "Humanization and Pharmacokinetics of a Monoclonal Antibody with Specificity for Both E- and P-selectin", *The American Association of Immunologists* (1998).

Helm, et al. "Identification of the high affinity receptor binding region in human immunoglobulin E", *J. Biol. Chem.* (1996) 271(13): 7494-500.

Hezareh, et al. "Effector Function Activities of a Panel of Mutants of a Broadly Neutralizing Antibody Against Human Immunodeficiency Virus Type", *J. Virol.* (2001) 75(24):12161-8.

Hornick, et al. "Single Amino Acid Substitution in the Fc Region of Chimeric TNT-3 Antibody Accelerates Clearance and Improves Immunoscintigraphy of Solid Tumors", *J. Nucl. Med.* (2000) 41(2):355-62.

Isaacs, et al. "Therapy with monoclonal antibodies. II. The contribution of Fc gamma receptor binding and the influence of C(H)1 and C(H)3 domains on in vivo effector function", *. J. Immunol.* (1998) 161(8):3862-9.

Ito, et al. "[An amino acid substitution determining G1m(x) allotypic]", *Nippon Hoigaku Zasshi* (1989) 43(2):155-60.

Jendeberg, et al. "Engineering of Fc(1) and Fc(3) from human immunoglobulin G to analyse subclass specificty for staphylococcal protein A", *J. Immunol Methods* (1997) 201(1):25-34.

Jollifee, "Humanized antibodies: enhancing therapeutic utility through antibody engineering", *Int. Rev. Immunol.* (1993) 10(2-3):241-50.

Kim, et al. "Mapping the site on human IgG for binding of the MHC class I-related receptor, FcRn", *Eur. J. Immunol.* (1999) 29:2819-2825.

Kim, et al. "Catabolism of the Murine IgG1 Molecule: Evidence that Both CH2-CH3 Domain Interfaces are Required for Persistence of IgG1 in the Circulation of Mice", *Scand. J. Immunol.*, (1994) 40:457-465.

Kim, et al. "Localization of the site of the murine IgG1 molecule that is involved in binding to the murine intestinal Fc receptor", *Eur. J. Immunol.* (1994) 24(10):2429-34.

Kostelny, et al. "Humanization and characterization of the anti-HLA-DR antibody 1D10", *Int. J. Cancer* (2001) 93:556-565.

Krueger, James G., et al. "Successful in vivo blockade of CD25 (high affinity interleukin 2 receptor) on T cells by administration of humanized anti-Tac antibody to patients with psoriasis", *J. Am. Acad. Dermatol.* (2000) 43(3):448-458.

Lund, et al. "Human Fc gamma RI and Fc gamma RII interact with distinct but overlapping sites on human IgG", *J. Immunol.* (1991) 147(8): 2657-62.

Lund, et al. "Multiple binding sites on the CD 2 domain of IgG for mouse Fc gamma R11", *Mol. Immunol.* (1992) 29(1):53-9.

Lund, et al. "Multple Interacts of IgG with its core oligosaccharide can modulate recognition by complment and human Fc gamma receptor 1 and influence the synthesis of its oligosaccharide chains", *J. Immunol.* (1996) 157(11): 4963-9.

Martin, W. L., et al. "Protein-Protein Recognition: The Neonatal Fc Receptor and Immunoglobulin G", Doctoral dissertation, Calfornia Institute of Technology.

McDonnell, et al. "The Structure of the IgE Cepsilon2 Domain and its Role in Stabilizing the Complex with its High-Affinity receptor FcepsilonRIalpha", *Nat. Struc. Biol.* (2001) 8(5):437-41.

Medesan, et al. "Comparative studies of rat IgG to furthur delineate the Fc:FcRn interaction site", *Eur. J. Immunol.* (1998) 28:2092-2100.

Medesan, et al. "Delineation of the amino acid residues involved in transcytosis and catabolism of mouse IgG1", *J. Immunol.* (1997) 158(5): 2211-7.

Morrison, et al. Sequences in Antibody Molecules Important for Receptor-Mediated Transport Into the Chicken Egg York, *Mol. Immunol.* (2002) 38(8):619-25.

Muraoka "Structural requirements for IgM assembly and cytolytic activity. Effects of mutations of the oligosaccharide acceptor site at Asn402", *J. Immunol.* (1989) 142(2):695-701.

Nagaoka, et al. "Single Amino Acid Sbustitution in the Mouse IgG1 Fc region induces drastic enhancement of the affinity to Protein A", *Protein Eng.*, (2003) 16(4):243-5.

Newman, et al. "Modification of the Fc Region of a Primatized IgG Antibody to Human CD4 Retain its Ability to Modulate CD4 Receptors But Does Not Deplete CD4(+) T Cells in Chimpanzees", *Clin. Immunol.* (2001) 98(2):164-74.

Ogata, et al. "Markedly prolonged incubation period of hepatitis B in a chimpanzee passively immunized with a human monoclonal antibody to the α determinant of hepatitis B surface antigen", *Proc. Natl. Acad. Sci. USA* (1993) 90:3014-3018.

Popov, et al. "The stolchiometry and affinity of the interaction of murine Fc fragments with the MHC class I-related receptor, FcRn", *Mol. Immunol.* (1996) 33(6):521-30.

Radaev, et al. "Recognition of Immunoglobulins by Fc gamma Receptors", *Mol. Immunol.* (2001) 38(14):1073-83.

Raghavan, et al. "Investigation of the interaction between the class I MHC-related Fc receptor and its immunoglobulin G ligand", *Immunity* (1994) 1:303-315.

Raghavan, et al. "Analysis of the pH dependence of the neonatal Fc receptor/immunoglobulin G interaction using antibody and receptor variants", *Biochemistry* (1995) 34(45):14649-57.

Reff, et al. "A review of modifications to recombinant antibodies: attempt to increase efficacy to oncology applications", *Critical Review in Oncology/Hematology* (2001) 40:25-35.

Saper, et al. "Refined structure of the human histocompatibility antigen HLA-A2 at 2.6 A resolution", *J. Mol. Biol.* (1991) 219:277-319.

Sarmay, et al. "Mapping and comparison of the interaction sites on the Fc region of IgG responsible for triggering antibody dependent cellular cytotoxicity (ADCC) through different types of human Fc gamma receptor", *Mol. Immunol.* (1992) 29(5):633-9.

Shields, et al. "High resolution mapping of the binding site of human IgG1 for Fc gamma RI, Fc gamma RII, Fc gamma RIII, and FcRn and design of IgG1 variants with improved binding to the Fc gamma R", *J. Biol. Chem.* (2001) 276:6591-6804.

Shopes, "A genetically engineered human IgG mutant with enhanced cytolytic activity", *J. Immunol.* (1992) 148(9):218-22.

Simister and Mostov, "An Fc receptor structurally related to MHC class I antigens", *Nature* (1989) 337:184-187.

Tao, "Studies of aglycosylated chimeric mouse-human IgG. Role of carbohydrate in the structure and effect functions mediated by the human IgG constant region", *J. Immunol.* (2002) 143(8):2595-601.

Taylor, et al. "In Vitro and in Vivo Activities of OX40 (CD134)-IgG Fusion Protein Isoforms with Different Levels of Immune-Effector Functions", *J. Leukoc. Biol.* (2002) 72(3):522-9.

Ward and Ghetie, "The effector functions of immunoglobulins: implications for therapy", *Ther. Immunol.* (1995) 2:77-94.

Ward, et al. "Evidence to Support the Cellular Mechanism Involved in Serum IgG Homeostasis in Humans", *Int'l Immunol.* (2003) 15(2):187-195.

Wawrzynczak, et al. "Recombinant mouse monoclonal antibodies with single amino acid substitutions affecting C1q and high affinity Fc receptor binding have identical serum half-lives in the BALB/c mouse", *Mol. Immunol.* (1992) 29(2):221-7.

Weng, et al. "Computational determination of the structure of rat Fc bound to the neonatal Fc receptor", *J. Mol. Biol.* (1998) 282:217-225.

West and Bjorkman, "Crystal structure and immunoglobulin G binding properties of the human major histocompatibility complex-related Fc receptor", *Biochemistry* (2000) 29:9698-9708.

Datta-Mannan, A., et al. "Humanized $IgG_1$ Variants With Differential Binding Properties to the Neonatal Fc Receptor: Relationship to Pharmacokinetics in Mice and Primates", *Drug Metabolism and Disposition*[published on Oct. 18, 2006 as doi:10.1124/dmd.106.011734—DMD#11734, pp. 1-47].

Datta-Mannan, A, et al. "Monoclonal Antibody Clearance: Impact of modulating the interaction of IgG with FcRn", *Journal of Biological Chemistry* [in press—published on Nov. 29, 2006 as Ms. M607161200, pp. 1-24].

Dall'Acqua, William F., et al. "Properties of Human IgG1s Engineered for Enhanced Binding to the Neonatal Fc Receptor (FcRn)", *Journal of Biological Chemistry* (2006) 281(33):23514-23524.

\* cited by examiner

ALTERATION OF FC-FUSION PROTEIN SERUM HALF-LIVES BY MUTAGENESIS

CROSS-REFERENCE TO RELATED APPLICATIONS

This application claims priority from U.S. Provisional Application No. 60/511,687, filed Oct. 15, 2003, and U.S. Provisional Application No. 60/562,627, filed Apr. 14, 2004, each of which is hereby incorporated herein by reference in its entirety.

FIELD OF THE INVENTION

The present invention relates to the fields of immunology and protein engineering. In particular, it concerns modified Fc-fusion proteins having altered binding affinities for FcRn and altered serum half-lives as a consequence of one or more amino acid modifications in the Fc region thereof.

BACKGROUND OF THE INVENTION

A native antibody molecule consists of two identical heavy chains, and two identical light chains. The heavy chain constant region includes $C_H1$, the hinge region, $C_H2$, and $C_H3$. Papain digestion of antibodies produces two fragments, Fab and Fc. The Fc fragment consists of $C_H2$, $C_H3$, and part of the hinge region. In human IgG molecules, the Fc fragment is generated by papain cleavage of the hinge region N-terminal to Cys 226. Therefore, the human IgG heavy chain Fc region is usually defined as stretching from the amino acid residue at position 226 to the C-terminus (numbered according to the EU index of Kabat et al., "Sequences of Proteins of Immunological Interest", $5^{th}$ ed., National Institutes of Health, Bethesda, Md. (1991); the EU numbering scheme is used hereinafter).

It has been recognized that the Fc region is critical for maintaining the serum half-life of an antibody of class IgG (Ward and Ghetie, Ther. Immunol. 2:77–94 (1995)). Studies have found that the serum half-life of an IgG antibody is mediated by binding of Fc to the neonatal Fc receptor (FcRn). FcRn is a heterodimer consisting of a transmembrane a chain and a soluble β chain (β2-microglobulin). FcRn shares 22–29% sequence identity with Class I MHC molecules and has a non-functional version of the MHC peptide-binding groove (Simister and Mostov, Nature 337: 184–187 (1989)). The α1 and α2 domains of FcRn interact with the $C_H2$ and $C_H3$ domains of the Fc region (Raghavan et al., Immunity 1:303–315 (1994)).

A model has been proposed for how FcRn might regulate the serum half-life of an antibody. According to this model, IgGs are taken up by endothelial cells through non-specific pinocytosis and then enter acidic endosomes. FcRn binds IgG at acidic pH (<6.5) in endosomes and releases IgG at basic pH (>7.4) in the bloodstream. Accordingly, FcRn salvages IgG from a lysosomal degradation pathway. When serum IgG levels decrease, more FcRn molecules are available for IgG binding so that an increased amount of IgG is salvaged. Conversely, if serum IgG levels rise, FcRn becomes saturated, thereby increasing the proportion of pinocytosed IgG that is degraded (Ghetie and Ward, Annu. Rev. Immunol. 18:739–766 (2000)).

Consistent with the above model, the results of numerous studies support a correlation between the affinity for FcRn binding and the serum half-life of an antibody (Ghetie and Ward, ibid.). Significantly, such a correlation has been extended to engineered antibodies with higher affinity for FcRn than their wild-type parent molecules. A large number of publications and patents based upon mutagenesis studies support this correlation (see e.g., Ghetie et al., Nat. Biotechnol. 15:637–640 (1997); Shields et al., J. Biol. Chem. 276:6591–6604 (2001); Dall'Acqua et al., J. Immunol. 169: 5171–5180 (2002); Hinton et al., J. Biol. Chem. 279:6213–6216 (2004); Kim et al., Eur. J. Immunol. 29:2819–2825 (1999); Hornick et al., J. Nucl. Med. 41:355–362 (2000); U.S. Pat. No. 6,165,745; U.S. Pat. No. 6,277,375 B1; U.S. Patent Application Publication No. 20020098193; PCT Publication WO 97/34621; and PCT Publication WO 02/060919). In addition, PCT Publication No. WO 98/05787 discloses deleting or substituting amino acids at positions 310–331 of the BR96 antibody in order to reduce its induced toxicity.

U.S. patent application Ser. No. 10/687,118, filed Oct. 15, 2003 (and hereby incorporated herein by reference in its entirety) and corresponding PCT Publication No. WO 04/035752 discloses mutations at positions 250, 314, and 428 of the Fc heavy chain constant region that provide modified antibodies with altered FcRn binding affinity and/or serum half-life relative to unmodified antibody.

Advances in molecular biology techniques have allowed the preparation of novel chimeric polypeptides with multiple functional domains. The most common of such chimeric polypeptides are immunoglobulin (Ig) fusion proteins. These proteins consist of the Fc regions of antibodies, typically mouse or human antibodies, fused to an unrelated protein or protein fragment. Such Fc-fusion proteins are valuable for studying protein function in vitro and in vivo and have potential therapeutic and diagnostic use in the clinical setting.

Methods for fusing or conjugating polypeptides to the constant regions of antibodies (i.e. making Fc fusion proteins) are described in, e.g., U.S. Pat. Nos. 5,336,603, 5,622,929, 5,359,046, 5,349,053, 5,447,851, 5,723,125, 5,783,181, 5,908,626, 5,844,095, and 5,112,946; EP 307, 434; EP 367,166; EP 394,827; PCT publications WO 91/06570, WO 96/04388, WO 96/22024; WO 97/34631, and WO 99/04813; Ashkenazi et al., Proc. Natl. Acad. Sci. USA 88:10535–10539 (1991); Traunecker et al., Nature 331: 84–86 (1988); Zheng et al., J. Immunol. 154:5590–5600 (1995); and Vil et al., Proc. Natl. Acad. Sci. USA 89:11337–11341 (1992), which are incorporated herein by reference in their entireties.

SUMMARY OF THE INVENTION

The present invention provides for modified Fc-fusion proteins having altered FcRn binding affinity and/or serum half-life relative to the corresponding unmodified Fc-fusion protein. The in vivo half-life (i.e., persistence in serum or other tissues of a subject) of Fc-fusion proteins, and other bioactive molecules, is an important clinical parameter that determines the amount and frequency of Fc-fusion protein (or any other pharmaceutical molecule) administration. Accordingly, such molecules, including Fc-fusion proteins, with increased (or decreased) half-life are of significant pharmaceutical importance.

The present invention relates to a modified molecule (preferably an Fc-fusion protein), that has an increased (or decreased) in vivo half-life by virtue of the presence of a modified IgG constant domain (preferably from a human IgG), or FcRn-binding portion thereof (preferably the Fc or hinge-Fc domain) wherein the IgG constant domain, or fragment thereof, is modified (preferably by an amino acid substitution) to increase (or decrease) the affinity for the FcRn.

In a particular embodiment, the present invention provides a modified class IgG Fc-fusion protein, whose in vivo half-life is extended (or reduced) by the changes in amino acid residues at positions identified by structural studies to be involved in the interaction of the hinge-Fc domain with the FcRn receptor. In preferred embodiments, the present invention provides a modified Fc-fusion protein with an in vivo mean elimination half-life at least about 1.3-fold longer than that of the corresponding unmodified Fc-fusion protein. It should be noted that the modified Fc-fusion proteins of the present invention may also exhibit altered (i.e., increase or decrease) bioavailability (e.g., transport to mucosal surfaces, or other target tissues) of the modified Fc-fusion proteins (or other molecules).

In preferred embodiments, the modified Fc-fusion protein (or fragment thereof) exhibits a higher affinity for FcRn at pH 6.0 than at pH 8.0. That is, the pH dependency of FcRn binding affinity mimics the wild-type pH dependency. In alternative embodiments, the modified Fc-fusion proteins of the present invention may exhibit altered pH dependence profiles relative to that of the unmodified Fc-fusion protein. Such altered pH dependence profiles are useful in therapeutic or diagnostic applications.

In some embodiments, the Fc-fusion protein modifications of the present invention will alter FcRn binding and/or serum half-life without altering other effector functions such as ADCC or CDC. In particularly preferred embodiments, the modified Fc-fusion proteins of the invention exhibit no changes in binding to Fc-gamma receptors or C1q. In alternative embodiments, the Fc-fusion protein modifications of the present invention may result in increased (or decreased) effector functions as well as increased serum half-life. In particularly preferred embodiments, the modified Fc-fusion proteins of the invention may have increased (or decreased) ADCC activities as well as increased serum half-life.

In preferred embodiments, the present invention provides for a modified Fc-fusion protein of class IgG, in which at least one amino acid from the heavy chain constant region selected from the group consisting of amino acid residues 250, 314, and 428 is substituted with an amino acid residue different from that present in the unmodified Fc-fusion protein. Preferably, this substitution alters the binding affinity for FcRn and/or the serum half-life of said modified Fc-fusion protein relative to the unmodified Fc-fusion protein. The present invention further provides for a modified Fc-fusion protein having an increased binding affinity for FcRn and an increased serum half-life as compared with the unmodified Fc-fusion protein, wherein amino acid residue 250 from the heavy chain constant region is substituted with glutamic acid or glutamine; or amino acid residue 428 from the heavy chain constant region is substituted with phenylalanine or leucine.

The present invention further provides for a modified Fc-fusion protein having an increased binding affinity for FcRn and/or an increased serum half-life as compared with the unmodified Fc-fusion protein, wherein (a) amino acid residue 250 from the heavy chain constant region is substituted with glutamic acid, and amino acid residue 428 from the heavy chain constant region is substituted with phenylalanine; (b) amino acid residue 250 from the heavy chain constant region is substituted with glutamine, and amino acid residue 428 from the heavy chain constant region is substituted with phenylalanine; or (c) amino acid residue 250 from the heavy chain constant region is substituted with glutamine, and amino acid residue 428 from the heavy chain constant region is substituted with leucine.

The present invention further provides for a modified Fc-fusion protein having a reduced binding affinity for FcRn and/or a reduced serum half-life as compared with the unmodified Fc-fusion protein, wherein amino acid residue 314 from the heavy chain constant region is substituted with another amino acid which is different from that present in an unmodified Fc-fusion protein.

The present invention further provides for a modified Fc-fusion protein having a reduced binding affinity for FcRn and/or a reduced serum half-life as compared with the unmodified Fc-fusion protein, wherein amino acid residue 250 from the heavy chain constant region is substituted with arginine, asparagine, aspartic acid, lysine, phenylalanine, proline, tryptophan, or tyrosine; or amino acid residue 428 from the heavy chain constant region is substituted with alanine, arginine, asparagine, aspartic acid, cysteine, glutamic acid, glutamine, glycine, histidine, lysine, proline, serine, threonine, tyrosine, or valine.

The present invention also provides for an Fc-fusion protein comprising a Fc-region, or constant region, substantially identical to that of a naturally occurring class IgG antibody, and wherein at least one amino acid residue selected from the group consisting of residues 250, 314, and 428 is different from that present in the naturally occurring class IgG antibody, thereby altering FcRn binding affinity and/or serum half-life of said Fc-fusion protein relative to a IgG Fc-fusion protein with the heavy constant region of the naturally occurring antibody. In preferred embodiments, naturally occurring class IgG antibody comprises a heavy chain constant region of a human IgG1, IgG2, IgG3 or IgG4 molecule. Also in preferred embodiments, amino acid residue 250 from the heavy chain constant region of the Fc-fusion protein having a constant region substantially identical to the naturally occurring class IgG antibody is glutamic acid or glutamine; or amino acid residue 428 from the heavy chain constant region is phenylalanine or leucine. In other preferred embodiments, the Fc-fusion protein having a constant region substantially identical to a naturally occurring class IgG antibody has a glutamic acid residue at position 250 and phenylalanine residue at position 428; or amino acid residue 250 is glutamine and amino acid residue 428 is phenylalanine; or amino acid residue 250 is glutamine and amino acid residue 428 is leucine.

In some embodiments, the Fc-fusion protein having a constant region substantially identical to a naturally occurring class IgG antibody constant region includes an amino acid residue at position 314 different from that present in the naturally occurring antibody, thereby reducing FcRn binding affinity and/or reducing serum half-life relative to the naturally occurring antibody. Embodiments include Fc-fusion proteins wherein amino acid residue 314 is alanine, arginine, aspartic acid, asparagine, cysteine, glutamic acid, glutamine, glycine, histidine, lysine, methionine, phenylalanine, proline, serine, threonine, tryptophan, tyrosine, or valine. In one preferred embodiment amino acid residue 314 is arginine.

In other embodiments, the Fc-fusion protein comprises an Fc region substantially identical to that present in a naturally occurring class IgG antibody constant region and includes an amino acid residue at position 250 selected from the group consisting of arginine, asparagine, aspartic acid, lysine, phenylalanine, proline, tryptophan, or tyrosine, thereby reducing FcRn binding affinity and/or reducing serum half-life relative to the naturally occurring antibody. Similarly, the amino acid residue at position 428 may be substituted with an amino acid residue selected from the group consisting of alanine, arginine, asparagine, aspartic acid, cysteine, glutamic acid, glutamine, glycine, histidine, lysine, proline, serine, threonine, tyrosine, or valine, thereby reducing FcRn binding affinity and/or reducing serum half-life relative to the naturally occurring antibody.

The present invention further provides for a method of modifying an Fc-fusion protein of class IgG, wherein said method comprises substituting at least one amino acid from the heavy chain constant region selected from the group consisting of amino acid residues 250, 314, and 428 with an amino acid which is different from that present in an unmodified Fc-fusion protein, thereby causing an alteration of the binding affinity for FcRn and/or the serum half-life of said unmodified Fc-fusion protein.

The present invention further provides for a method of producing a modified Fc-fusion protein of class IgG with an altered binding affinity for FcRn and/or an altered serum half-life as compared with an unmodified Fc-fusion protein, wherein said method comprises:

(a) preparing an expression vector (preferably a replicable expression vector) comprising a suitable promoter operably linked to DNA encoding at least a constant region of an immunoglobulin heavy chain wherein at least one amino acid from the heavy chain constant region selected from the group consisting of amino acid residues 250, 314, and 428 is substituted with an amino acid which is different from that present in an unmodified Fc-fusion protein thereby causing an alteration in FcRn binding and/or serum half-life;

(b) transforming host cells with said vector; and (c) culturing said transformed host cells to produce said modified Fc-fusion protein.

The present invention also provides a modified IgG class antibody fragment comprising a heavy chain constant region or Fc-region, wherein at least one amino acid residue selected from the group consisting of residues 250, 314, and 428 is different from that present in the unmodified IgG class antibody.

In another embodiment the invention provides a modified IgG class antibody fragment comprising a heavy chain constant region or Fc region substantially identical to that of a naturally occurring class IgG antibody, wherein at least one amino acid residue selected from the group consisting of residues 250, 314, and 428 is different from that present in the naturally occurring class IgG antibody.

The present invention provides polynucleotide sequences encoding the polypeptide molecules of the modified Fc-fusion proteins described herein. In one embodiment, the invention provides the polynucleotide molecules encoding partial or full heavy chains of a IgG class antibody, such as the constant regions, Fc regions, or $C_H2$-$C_H3$ regions, that have been modified with the mutations (substitutions) described herein. In another embodiment, the invention provides an isolated polynucleotide molecule encoding a polypeptide comprising a sequence at least 90% identical to a sequence selected from SEQ ID NOs: 1–57.

The present invention also provides amino acid sequences encoding the polypeptide molecules of the modified Fc-fusion proteins described herein. In a preferred embodiment, the invention provides an isolated polypeptide comprising an amino acid sequence at least 90% identical to a sequence selected from SEQ ID NOs: 1–57.

The present invention also provides a vector comprising a polynucleotide molecule encoding a modified Fc-fusion protein as described above, or the polynucleotide molecules encoding the modified partial or full heavy chains of a IgG class antibody, such as the constant regions, Fc regions or $C_H2$-$C_H3$ regions, with the mutations (substitutions) described herein.

The present invention includes a host cell transfected with a vector comprising said polynucleotide molecules as described herein. In preferred embodiments, the host cells comprising the nucleic acid encoding a modified Fc-fusion protein described herein are derived from prokaryotic organisms such as *Escherichia coli*, or eukaryotic multi-cellular organisms, including yeasts, plants, insects, and mammals.

The present invention also includes pharmaceutical compositions and methods of prophylaxis and therapy using modified Fc-fusion proteins, proteins and other bioactive molecules of the invention having altered half-lives. Also included are methods of diagnosis using modified Fc-fusion proteins, proteins and other bioactive molecules of the invention having altered half-lives. In preferred embodiments, the amino acid modifications of the present invention may be used to extend the serum half-life of a therapeutic or diagnostic Fc-fusion protein. For example, the present invention provides for a modified therapeutic or diagnostic Fc-fusion protein of class IgG with an in vivo elimination half-life at least about 1.3-fold longer than that of the corresponding unmodified Fc-fusion protein. In preferred embodiments the modified therapeutic or diagnostic Fc-fusion protein has an in vivo elimination half-life at least about 1.5-fold, 1.8-fold, 1.9-fold, or greater than 2.0-fold longer than that of the corresponding unmodified Fc-fusion protein. In alternative preferred embodiments, the amino acid modifications of the present invention may also be used to reduce the serum half-life of a therapeutic or diagnostic Fc-fusion protein. Such therapeutic or diagnostic Fc-fusion proteins are well-known in the art and listed in the following description of the invention.

DETAILED DESCRIPTION OF THE PREFERRED EMBODIMENTS

Figure 1:
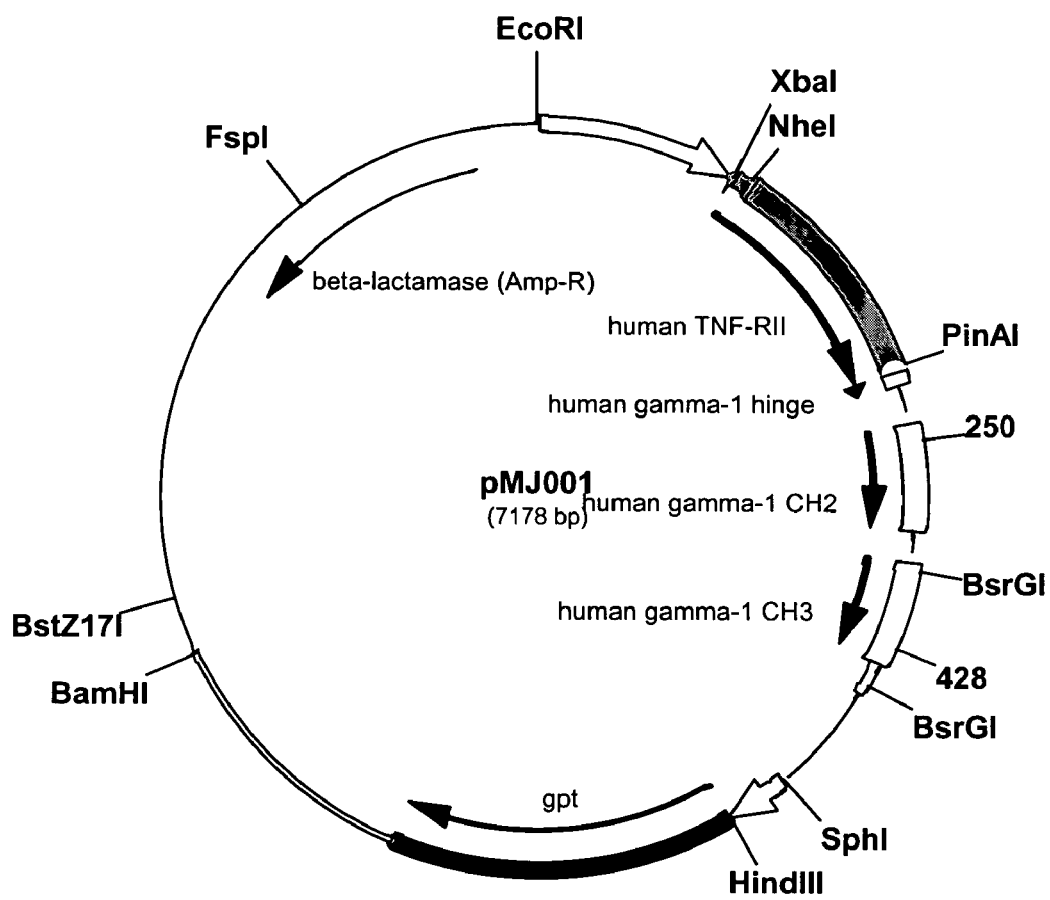
FIG. 1. Restriction Map of Fc-Fusion Vector pMJ001
FIG. 2. Restriction Map of Fc-Fusion Vector pMJ026
FIG. 3. Restriction Map of Fc-Fusion Vector pMJ041
FIG. 4. Restriction Map of Human FcRn Vector pDL208

I. Modified Fc-Fusion Proteins with Altered FcRn Binding Affinity and/or Serum Half-Lives In order that the invention may be more completely understood, several definitions are set forth.

As used herein, the terms "immunoglobulin" and "antibody" refer to proteins consisting of one or more polypeptides substantially encoded by immunoglobulin genes. The recognized immunoglobulin genes include the kappa, lambda, alpha, gamma (γ1, γ2, γ3, γ4), delta, epsilon, and mu constant region genes, as well as the myriad immunoglobulin variable region genes. Full-length immunoglobulin "light chains" (about 25 kDa or 214 amino acids) are encoded by a kappa or lambda variable region gene at the NH2-terminus (about 110 amino acids) and a kappa or lambda constant region gene at the COOH-terminus. Full-length immunoglobulin "heavy chains" (about 50 kDa or 446 amino acids) are similarly encoded by a heavy chain variable region gene (about 116 amino acids) and one of the other aforementioned constant region genes, e.g., gamma (encoding about 330 amino acids).

One form of antibody is a tetramer consisting of two identical pairs of immunoglobulin chains, each pair having one light and one heavy chain. In each pair, the light and heavy chain variable regions are together responsible for binding to an antigen, and the constant regions are responsible for the antibody effector functions. In addition to tetrameric antibodies, immunoglobulins may exist in a variety of other forms including, for example, Fv, Fab, and (Fab')$_2$, as well as bifunctional hybrid antibodies (e.g., Lanzavecchia and Scheidegger, Eur. J. Immunol. 17:105–111 (1987)) and in single chains (e.g., Huston et al., Proc. Natl. Acad. Sci. USA 85:5879–5883 (1988), and Bird et al., Science 242:423–426 (1988), each of which is hereby incorporated by reference herein).

As used herein, the term "antibody" term also includes genetically engineered or otherwise modified forms of immunoglobulins, such as chimeric antibodies, humanized antibodies, heteroconjugate antibodies (e.g., bispecific antibodies, diabodies, triabodies, and tetrabodies), and antigen binding fragments of antibodies, including e.g., Fab', F(ab')$_2$, Fab, Fv, rIgG, and scFv fragments. The term also includes genetically engineered or otherwise modified forms of immunoglobulins, such as chimeric antibodies, humanized antibodies, heteroconjugate antibodies (e.g., bispecific antibodies, diabodies, triabodies, and tetrabodies), and antigen binding fragments of antibodies, including e.g., Fab', F(ab')$_2$, Fab, Fv, rIgG, and scFv fragments.

As used herein, "human" antibodies include antibodies having the amino acid sequence of a human immunoglobulin and includes antibodies isolated from human immunoglobulin libraries or from animals transgenic for one or more human immunoglobulin and that do not express endogenous immunoglobulins, as described infra, and, for example; in U.S. Pat. No. 5,939,598 (Kucherlapati et al.), which is hereby incorporated by reference herein.

"Antibodies of IgG class" as used herein refers to antibodies of IgG1, IgG2, IgG3, and IgG4. The numbering of the amino acid residues in the heavy and light chains is that of the EU index (Kabat, et al., "Sequences of Proteins of Immunological Interest", 5$^{th}$ ed., National Institutes of Health, Bethesda, Md. (1991); the EU numbering scheme is used herein).

A "fusion protein" as used herein refers to an expression product resulting from the fusion of at least two genes. An "Fc-fusion protein" is a chimeric polypeptide comprising the Fc-region, or constant region, of an antibody fused, or conjugated, to an unrelated protein or protein fragment.

The present invention provides "modified" Fc fusion proteins wherein the amino acid sequence of the Fc region has been altered relative to the amino acid sequence of the Fc- or constant region found in a naturally occurring, or previously modified (e.g. chimeric), antibody. For example, a previously designed, functional Fc-fusion proteins (i.e. an "unmodified" Fc-fusion protein) may be further engineered (i.e. "modified") with mutations according to the present invention in order to obtain the desired characteristics of FcRn binding affinity and/or serum half-life. The possible variants of altered Fc-fusion proteins useful with the present invention are many and range from the changing of just one or a few amino acids to the complete redesign of, for example, the constant region. Changes in the constant region will, in general, be made in order to improve, or alter (i.e. increase or decrease) characteristics, such as binding interactions with various Fc-gamma receptors and/or other immunoglobulin effector functions. In a preferred embodiment, the present invention provides "modified" Fc-fusion proteins having an altered serum half-life or FcRn binding affinity relative to the unmodified Fc-fusion protein.

The present invention may be used to create "modified" (i.e. mutant) Fc-fusion proteins wherein the Fc-domain is derived from the Fc-region or constant region of a "naturally occurring" antibody of any species. A "naturally occurring" antibody refers to an antibody produced by a host animal. Non-limiting exemplary "naturally occurring" antibodies of the present invention include antibodies produced by humans, chickens, goats, and rodents (e.g., rats, mice, hamsters and rabbits), and includes transgenic rodents genetically engineered to produce human antibodies (see, e.g., Lonberg et al., WO 93/12227; U.S. Pat. No. 5,545,806; and Kucherlapati et al., WO 91/10741; U.S. Pat. No. 6,150,584, which are hereby incorporated herein by reference in their entirety).

The "modified" Fc-fusion proteins of the present invention also may be engineered from "unmodified" Fc-fusion proteins derived from genetically-altered antibodies that are functionally equivalent to the corresponding naturally occurring antibodies (e.g. chimeric, humanized, or primatized antibodies). Fc-fusion proteins derived from antibodies that are genetically-altered to provide improved stability and/or therapeutic efficacy are preferred. Examples of genetically-altered antibodies include those with conservative substitutions of amino acid residues, and one or more deletions or additions of amino acids that do not significantly deleteriously alter the functional or binding utility. Substitutions can range from changing or modifying one or more amino acid residues to complete redesign of a region as long as the binding or functional utility is maintained. Fc-fusion proteins of this invention can be altered post-translationally (e.g., acetylation, and phosphorylation) or can be altered synthetically (e.g., the attachment of a labeling group).

The present invention also may be used to create "modified" Fc-fusion proteins engineered from "unmodified" Fc-fusion proteins whose bioactive sites, such as ligand-binding sites, Fc-receptor binding sites, or complement-binding sites, have been previously modified by genetic engineering to increase or reduce such activities compared to the wild-type.

In addition, the present invention may be used to create "modified" Fc-fusion proteins with Fc domains derived from recombinant antibodies having the same amino acid sequences as a natural antibody. They can be made in any expression systems including both prokaryotic and eukaryotic expression systems or using phage display methods (see, e.g., Dower et al., WO 91/17271 and McCafferty et al., WO 92/01047; U.S. Pat. No. 5,969,108, which are herein incorporated by reference in their entirety).

An "Fc-fusion protein having a constant region substantially identical to a naturally occurring class IgG antibody constant region," as used herein refers to an Fc-fusion protein in which any constant region present is substantially identical, i.e. at least about 85–90%, and preferably at least 95% identical, to the amino acid sequence of the naturally occurring class IgG antibody's constant region.

The terms "identical" or percent "identity," in the context of two or more amino acid or nucleotide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., description of BLAST at NCBI web site located on the worldwide web at ncbi.nlm.nih.gov). Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. The well-known algorithms for measuring sequence identity can account for gaps and the like. Preferably, identity exists over a region that is at least about 25 amino acids or nucleotides in length, or more preferably over a region that is 50–100 amino acids or nucleotides in length.

The Fc-fusion proteins of the present invention may comprise any of the recognized immunoglobulin isotypes, but the four IgG isotypes are preferred, with IgG1 and IgG2 especially preferred. In one embodiment, the invention also provides the isolated polynucleotides encoding a polypeptide, or the isolated polypeptide, comprising the heavy chain constant region, or Fc-region, modified with one or more of the amino acid substitutions disclosed herein. These isolated polynucleotides or polypeptides corresponding to modified IgG antibody fragments may then be used to generate the modified Fc-fusion proteins. Fc-fusion proteins derived from antibodies with constant regions mutated to have reduced effector functions, for example the IgG2M3 and other IgG2 mutants described in U.S. Pat. No. 5,834,597 (which is incorporated by reference herein in its entirety), are included. In a preferred aspect, the unmodified and modified Fc-fusion proteins of the present invention comprise heavy chain constant regions of human IgGs, preferably IgG1, IgG2, IgG2M3, IgG3, and IgG4.

In addition, the "modified" Fc-fusion proteins of the invention may comprise an Fc region from an IgG subclass of any given animals. For example, in humans, the IgG classes including IgG1, IgG2, IgG3, and IgG4; in mouse the IgG classes including IgG1, IgG2a, IgG2b, and IgG3; and in rat the IgG classes including IgG1, IgG2a, IgG2b, IgG2c, and IgG3. It is known that certain IgG subclasses, for example, rat IgG2b and IgG2c, have higher clearance rates than, for example, IgG1 (Medesan et al., Eur. J. Immunol. 28:2092–2100 (1998)). Thus, when using IgG subclasses other than IgG1 it may be advantageous to substitute one or more of the residues, particularly in the $C_H2$ and $C_H3$ domains, which differ from the IgG1 sequence with those of IgG1, thereby increasing the in vivo half-life of the other types of IgG.

The unrelated protein or protein fragment (i.e. the non-immunoglobulin part) used to create the "modified" Fc-fusion protein of the present invention may be from any animal origin including birds and mammals. Preferably, the proteins are derived from human, rodent, donkey, sheep, rabbit, goat, guinea pig, camel, horse, or chicken antibodies.

Among the "modified" Fc-fusion proteins provided by the present invention are those of class IgG (i.e. IgG1, IgG2, IgG3, and IgG4 antibodies) in which at least one amino acid from the IgG heavy chain constant region selected from the group consisting of amino acid residues 250, 314, and 428, is substituted with another amino acid which is different from that present in the unmodified Fc-fusion protein. The numbering of the residues in the heavy chain is that of the EU index (Kabat et al., op. cit.). According to the present invention, substitutions may be made at position 250, 314, or 428 alone, or in any combinations thereof, such as at positions 250 and 428, or at positions 250 and 314, or at positions 314 and 428, or at positions 250, 314, and 428, with positions 250 and 428 as a preferred combination. For each position, the substituting amino acid may be any amino acid residue different from that present in that position of the unmodified Fc-fusion protein. Modification at one or more of these sites, according to the present invention, thereby alters the binding affinity for FcRn and/or the serum half-life of the modified Fc-fusion protein compared to the binding affinity and/or serum half-life of said unmodified Fc-fusion protein.

For position 314, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine.

For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine.

For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine.

The present invention provides for modified Fc-fusion proteins comprising at least one of the above-described amino acid substitutions. For example, the present invention provides for the mutated IgG1 constant regions comprising two of the above-mentioned substitutions at position 250, 314, and/or 428. The amino acid sequences of some specific substitutions (i.e. mutations) of the constant region provided by the present invention are disclosed in Table 1 (SEQ ID NOs: 1–57).

TABLE 1

| Substituting Amino Acid | 250 | 314 | 428 |
|---|---|---|---|
| Alanine (A) | T250A; SEQ ID NO: 1 | L314A; SEQ ID NO: 20 | M428A; SEQ ID NO: 39 |
| Cysteine (C) | T250C; SEQ ID NO: 2 | L314C; SEQ ID NO: 21 | M428C; SEQ ID NO: 40 |
| Aspartic acid (D) | T250D; SEQ ID NO: 3 | L314D; SEQ ID NO: 22 | M428D; SEQ ID NO: 41 |
| Glutamic acid (E) | T250E; SEQ ID NO: 4 | L314E; SEQ ID NO: 23 | M428E; SEQ ID NO: 42 |
| Phenylalanine (F) | T250F; SEQ ID NO: 5 | L314F; SEQ ID NO: 24 | M428F; SEQ ID NO: 43 |
| Glycine (G) | T250G; SEQ ID NO: 6 | L314G; SEQ ID NO: 25 | M428G; SEQ ID NO: 44 |

TABLE 1-continued

| Substituting Amino Acid | 250 | 314 | 428 |
|---|---|---|---|
| Histidine (H) | T250H; SEQ ID NO: 7 | L314H; SEQ ID NO: 26 | M428H; SEQ ID NO: 45 |
| Isoleucine (I) | T250I; SEQ ID NO: 8 | L314I; SEQ ID NO: 27 | M428I; SEQ ID NO: 46 |
| Lysine (K) | T250K; SEQ ID NO: 9 | L314K; SEQ ID NO: 28 | M428K; SEQ ID NO: 47 |
| Leucine (L) | T250L; SEQ ID NO: 10 | Wild Type | M428L; SEQ ID NO: 48 |
| Methionine (M) | T250M; SEQ ID NO: 11 | L314M; SEQ ID NO: 29 | Wild Type |
| Asparagine (N) | T250N; SEQ ID NO: 12 | L314N; SEQ ID NO: 30 | M428N; SEQ ID NO: 49 |
| Proline (P) | T250P; SEQ ID NO: 13 | L314P; SEQ ID NO: 31 | M428P; SEQ ID NO: 50 |
| Glutamine (Q) | T250Q; SEQ ID NO: 14 | L314Q; SEQ ID NO: 32 | M428Q; SEQ ID NO: 51 |
| Arginine (R) | T250R; SEQ ID NO: 15 | L314R; SEQ ID NO: 33 | M428R; SEQ ID NO: 52 |
| Serine (S) | T250S; SEQ ID NO: 16 | L314S; SEQ ID NO: 34 | M428S; SEQ ID NO: 53 |
| Threonine (T) | Wild Type | L314T; SEQ ID NO: 35 | M428T; SEQ ID NO: 54 |
| Valine (V) | T250V; SEQ ID NO: 17 | L314V; SEQ ID NO: 36 | M428V; SEQ ID NO: 55 |
| Tryptophan (W) | T250W; SEQ ID NO: 18 | L314W; SEQ ID NO: 37 | M428W; SEQ ID NO: 56 |
| Tyrosine (Y) | T250Y; SEQ ID NO: 19 | L314Y; SEQ ID NO: 38 | M428Y; SEQ ID NO: 57 |

The "modified" Fc-fusion proteins of the present invention have many uses, including in vivo use of the modified Fc-fusion proteins in humans and in vitro detection assays, it may be preferable to use human Fc-fusion proteins that have been modified (i.e., mutated) according to the present invention.

For example, the present invention permits modification of therapeutic Fc-fusion proteins to increase the in vivo half-life, allowing administration of lower effective dosages and/or less frequent dosing of the therapeutic Fc-fusion proteins. Such modification to increase in vivo half-life can also be useful to improve diagnostic Fc-fusion proteins as well. For example, increased serum half-life of a diagnostic Fc-fusion protein may permit administration of lower doses to achieve sufficient diagnostic sensitivity. Alternatively, decreased serum half-life may be advantageous in applications where rapid clearance of a diagnostic Fc-fusion protein is desired.

The present invention provides for a modified Fc-fusion protein having an increased binding affinity for FcRn and/or an increased serum half-life as compared with the unmodified Fc-fusion protein, wherein amino acid residue 250 or 428 from the heavy chain constant region is substituted with another amino acid residue that is different from that present in the unmodified Fc-fusion protein. Preferably, amino acid residue 250 from the heavy chain constant region is substituted with glutamic acid or glutamine. Alternatively, amino acid residue 428 from the heavy chain constant region is substituted with phenylalanine or leucine.

In one example, said unmodified Fc-fusion protein comprises the heavy chain constant region of an IgG1, or IgG2, or IgG2M3, or IgG3, or IgG4 molecule. IgG1, IgG2, IgG2M3, IgG3, and IgG4 have a threonine residue at position 250 and a methionine residue at position 428. According to the present invention, preferably, the threonine residue at position 250 is substituted with glutamic acid (T250E) or glutamine (T250Q), and the methionine residue at position 428 is substituted with phenylalanine (M428F) or leucine (M428L).

The present invention provides for a modified Fc-fusion protein having an increased binding affinity for FcRn and/or an increased serum half-life as compared with the unmodified Fc-fusion protein and/or the modified Fc-fusion proteins having the above-described amino acid substitutions at position 250 or position 428 alone. The amino acid modification can be any one of the following substitutions:

1) amino acid residue 250 from the heavy chain constant region is substituted with glutamic acid and amino acid residue 428 from the heavy chain constant region is substituted with phenylalanine;
2) amino acid residue 250 from the heavy chain constant region is substituted with glutamine and amino acid residue 428 from the heavy chain constant region is substituted with phenylalanine;
3) amino acid residue 250 from the heavy chain constant region is substituted with glutamine and amino acid residue 428 from the heavy chain constant region is substituted with leucine.

In a preferred embodiment of the present invention, the binding affinity for FcRn and/or the serum half-life of the modified Fc-fusion protein is increased by at least about 30%, 50%, 80%, 2 fold, 3 fold, 4 fold, 5 fold, 10 fold, 15 fold, 20 fold, 25 fold, 30 fold, 40 fold, 50 fold, 60 fold, 70 fold, 80 fold, 90 fold, or 100 fold.

Alternatively, the present invention provides for a modified Fc-fusion protein having a reduced binding affinity for FcRn and/or a reduced serum half-life as compared with the unmodified Fc-fusion protein, wherein amino acid residue 314 from the heavy chain constant region is substituted with another amino acid which is different from that present in an unmodified Fc-fusion protein. The modified Fc-fusion proteins having an amino acid substitution at position 314 have been shown to display a reduced binding affinity, suggesting that position 314 should be modified if a reduced serum half-life of an antibody is desired. Preferably, the amino acid residue 314 from the heavy chain constant region is substituted with alanine, arginine, asparagine, aspartic acid, cysteine, glutamic acid, glutamine, glycine, histidine, lysine, methionine, phenylalanine, proline, serine, threonine, tryptophan, tyrosine, or valine. More preferably, the amino acid substitution is from leucine to alanine or arginine at position 314.

II. Production of Modified Fc-Fusion Proteins with Altered FcRn Binding Affinity and/or Serum Half-Lives The present invention provides for methods of producing modified Fc-fusion proteins with altered FcRn binding affinity and/or serum half-lives. Generally, the methods involve modifying a given Fc-fusion protein of class IgG by substituting amino acids at one or more of the positions disclosed herein (e.g. amino acid residues 250, 314, and 428). These modifications may be achieved chemically, or by random or site-directed mutagenesis using standard recombinant DNA technology. For example, site-directed mutagenesis may be used to introduce the amino acid substitutions into the DNA encoding an unmodified Fc-fusion protein. Then, the resulting mutant DNAs are inserted into an expression vector, delivered into host cells, where the modified fusion proteins are produced, secreted and ultimately purified.

Fc-Fusion Proteins

Fusion proteins useful with the methods of the present invention may be produced by standard recombinant DNA techniques or by protein synthetic techniques, e.g., by use of a peptide synthesizer. For example, a nucleic acid molecule encoding a fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., "Current Protocols in Molecular Biology", Ausubel et al., eds., John Wiley & Sons, (1992)). Moreover, a nucleic acid encoding a bioactive molecule can be cloned into an expression vector containing the Fc domain or a fragment thereof such that the bioactive molecule is linked in-frame to the constant domain or fragment thereof.

Methods for fusing or conjugating polypeptides to the constant regions of antibodies are known in the art. See, e.g., U.S. Pat. Nos. 5,336,603, 5,622,929, 5,359,046, 5,349,053, 5,447,851, 5,723,125, 5,783,181, 5,908,626, 5,844,095, and 5,112,946; European Patent publications, EP 0 307 434; EP 0 367 166; EP 0 394 827; PCT publications WO 91/06570, WO 96/04388, WO 96/22024, WO 97/34631, and WO 99/04813; Ashkenazi et al., Proc. Natl. Acad. Sci. USA 88:10535–10539 (1991); Traunecker et al., Nature 331: 84–86 (1988); Zheng et al., J. Immunol. 154:5590–5600 (1995); and Vil et al., Proc. Natl. Acad. Sci. USA 89:11337–11341 (1992), each of which is incorporated herein by reference in its entirety.

Nucleotide sequences encoding bioactive protein molecules that may be used with the methods of the present invention may be obtained from any information available to those of skill in the art (e.g., from Genbank, the literature, or by routine cloning), and the nucleotide sequence encoding a constant domain or a fragment thereof with increased affinity for the FcRn may be determined by sequence analysis of mutants produced using techniques described herein, or may be obtained from Genbank or the literature. The nucleotide sequence coding for a fusion protein can be inserted into an appropriate expression vector, i.e., a vector that contains the necessary elements for the transcription and translation of the inserted protein-coding sequence. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Modification of a Fc-Fusion Protein

Generally, a modified Fc-fusion protein with altered in vivo stability, DNA segments encoding such proteins may be created by operatively incorporated into a recombinant vector, in frame with the constant region of a modified antibody, whether upstream or downstream, in a position so as to render the vector capable of expressing a fusion protein comprising such a protein operably linked with the constant region. Techniques for the manipulation of DNA segments in this manner, for example, by genetic engineering using restriction endonucleases, will be known to those of skill in the art in light of both the present disclosure and references such as Sambrook and Russell, "Molecular Cloning: A Laboratory Manual", $3^{rd}$ edition, Cold Spring Harbor Laboratory Press, New York (2001).

Preferably, a modified Fc-fusion protein of class IgG with an altered binding affinity for FcRn and an altered serum half-life as compared with unmodified Fc-fusion protein may be produced by the method comprising:

(a) preparing a replicable expression vector comprising a suitable promoter operably linked to a DNA which encodes at least a constant region of an immunoglobulin heavy chain and a suitable fusion moiety and in which at least one amino acid from the heavy chain constant region selected from the group consisting of amino acid residues 250, 314, and 428 is substituted with an amino acid which is different from that present in an unmodified heavy chain thereby causing an alteration in FcRn binding and/or serum half-life;

(b) transforming host cells with said vector; and (c) culturing said transformed host cells to produce said modified Fc-fusion protein.

To generate the DNA in Step (a), the amino acid substitutions can be introduced by mutagenesis, including, but not limited to, site-directed mutagenesis (Kunkel, Proc. Natl. Acad. Sci. USA 82:488–492 (1985)), PCR mutagenesis (Higuchi, in "PCR Protocols: A Guide to Methods and Applications", Academic Press, San Diego, pp. 177–183 (1990)), and cassette mutagenesis (Wells et al., Gene 34:315–323 (1985)). Preferably, site-directed mutagenesis is performed by the overlap-extension PCR method, which is disclosed in the Examples (Higuchi, in "PCR Technology: Principles and Applications for DNA Amplification", Stockton Press, New York, pp. 61–70 (1989)).

The technique of overlap-extension PCR (Higuchi, ibid.) can be used to introduce any desired mutation(s) into a target sequence (the starting DNA). For example, the first round of PCR in the overlap-extension method involves amplifying the target sequence with an outside primer (primer 1) and an internal mutagenesis primer (primer 3), and separately with a second outside primer (primer 4) and an internal primer (primer 2), yielding two PCR segments (segments A and B). The internal mutagenesis primer (primer 3) is designed to contain mismatches to the target sequence specifying the desired mutation(s). In the second round of PCR, the products of the first round of PCR (segments A and B) are amplified by PCR using the two outside primers (primers 1 and 4). The resulting full-length PCR segment (segment C) is digested with restriction enzymes and the resulting restriction fragment is cloned into an appropriate vector.

As the first step of mutagenesis, the starting DNA is operably cloned into a mutagenesis vector. The primers are designed to reflect the desired amino acid substitution. In one example, the vectors used for in vitro mutagenesis can be used for directing protein expression. Thus, the resulting DNA of the overlap-extension PCR can be cloned back into the mutagenesis vector so that an expression vector comprising the DNA with the desired mutation is created. The starting DNA can be a DNA encoding an entire unmodified Fc-fusion protein, an entire immunoglobulin heavy chain of an unmodified Fc-fusion protein, the constant region of a heavy chain, or part of the heavy chain constant region of an unmodified Fc-fusion protein as long as the amino acid residue that is going to be modified is included.

If the DNA encoding an entire unmodified Fc-fusion protein is used as the starting DNA for mutagenesis, the entire modified Fc-fusion protein can be produced by performing Steps (a), (b), and (c) of the method described herein. If the starting DNA for mutagenesis is a DNA encoding part of the heavy chain constant region, such as a $C_H2$-$C_H3$ segment or an Fc domain, the resulting DNA encoding such a modified partial heavy chain is first connected in frame with the remaining fusion moiety, so that the DNA encoding an Fc-fusion protein with the modification described herein in Step (a) is generated. The connection of the DNA encoding the modified partial heavy chain and the remaining fusion moiety can be achieved by using the standard molecular cloning techniques known in the art of molecular biology, such as restriction digestions and ligations (Sambrook and Russell, "Molecular Cloning: A Laboratory Manual", $3^{rd}$ edition, Cold Spring Harbor Laboratory Press, New York (2001)).

Generally, the DNA segments encoding Fc-fusion proteins may be operably linked to control sequences in the expression vector(s) that ensure the expression of immunoglobulin polypeptides. Such control sequences include a signal sequence, a promoter, an enhancer, and a transcription termination sequence (see Queen et al., Proc. Natl. Acad. Sci. USA 86:10029–10033 (1989); WO 90/07861; Co et al., J. Immunol. 148:1149–1154 (1992); "Antibody Engineering: A Practical Guide", Borrebaeck, Ed., Freeman, N.Y. (1997)) which are incorporated herein by reference in their entirety for all purposes). Further methods and strategies for expression systems and regulation are discussed below.

Host cells are transformed by using the techniques known in the art, such as liposome, calcium phosphate, electroporation, etc. (Sambrook and Russell, op. cit.). Preferably, the host cells are transiently transfected using the liposome method. More preferably, the host cells are stably transfected using the electroporation method. The host cells used to produce the modified Fc-fusion proteins of the present invention may be cultured in a variety of media known in the arts.

Expression Systems for Fc-Fusion Proteins

*E. coli* is one prokaryotic host particularly useful for cloning and/or expressing the DNA sequences of the present invention. Other microbial hosts suitable for use include bacilli, such as *Bacillus subtilis*, and other *enterobacteriaceae*, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters can be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation.

Other microbes, such as yeast, can also be used for expression. *Saccharomyces* is a preferred host, with suitable vectors having expression control sequences, such as promoters, including 3-phosphoglycerate kinase or other glycolytic enzymes, and an origin of replication, termination sequences and the like as desired.

Plants and plant cell cultures can be used for expression of the DNA sequence of the invention (Larrick and Fry, Hum. Antibodies Hybridomas 2:172–189 (1991); Benvenuto et al., Plant Mol. Biol. 17:865–874 (1991); During et al., Plant Mol. Biol. 15:281–293 (1990); Hiatt et al., Nature 342:76–78 (1989)). Preferable plant hosts include, for example: *Arabidopsis, Nicotiana tabacum, Nicotiana rustica*, and *Solanum tuberosum*. A preferred expression cassette for expressing polynucleotide sequences encoding the modified Fc-fusion proteins of the invention is the plasmid pMOG18 in which the inserted polynucleotide sequence encoding the modified Fc-fusion protein is operably linked to a CaMV 35 S promoter with a duplicated enhancer; pMOG18 is used according to the method of Sijmons et al., Bio/Technology 8:217–221 (1990). Alternatively, a preferred embodiment for the expression of modified Fc-fusion proteins in plants follows the methods of Hiatt et al., supra, with the substitution of polynucleotide sequences encoding the modified Fc-fusion proteins of the invention for the immunoglobulin sequences used by Hiatt et al., supra. *Agrobacterium tumifaciens* T-DNA-based vectors can also be used for expressing the DNA sequences of the invention; preferably such vectors include a marker gene encoding spectinomycin-resistance or another selectable marker.

Insect cell culture can also be used to produce the modified Fc-fusion proteins of the invention, typically using a baculovirus-based expression system. The modified Fc-fusion proteins can be produced by expressing polynucleotide sequences encoding the modified Fc-fusion proteins according to the methods of Putlitz et al., Bio/Technology 8:651–654 (1990).

In addition to microorganisms and plants, mammalian cell culture can also be used to express and produce the polypeptides of the present invention (see "From Genes to Clones", Winnacker, VCH Publishers, New York (1987)). Mammalian cells are actually preferred, because a number of suitable host cell lines capable of secreting intact Fc-fusion proteins have been developed in the art, and include the CHO cell lines, various COS cell lines, HeLa cells, preferably myeloma cell lines, etc., or transformed B-cells or hybridomas. Expression vectors for these cells can include expression control sequences, such as an origin of replication, a promoter, an enhancer (Queen et al., Immunol. Rev. 89:49–68 (1986)), and necessary processing information sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, cytomegalovirus and the like. Generally, a selectable marker, such as a neo expression cassette, is included in the expression vector.

The expression of a fusion protein may be controlled by any promoter or enhancer element known in the art. Promoters which may be used to control the expression of the gene encoding fusion protein include, but are not limited to, the SV40 early promoter region (Bernoist and Chambon, Nature 290:304–310 (1981)), the promoter contained in the 3' long terminal repeat of Rous sarcoma virus (Yamamoto et al., Cell 22:787–797 (1980)), the herpes thymidine kinase promoter (Wagner et al., Proc. Natl. Acad. Sci. USA 78:1441–1445 (1981)), the regulatory sequences of the metallothionein gene (Brinster et al., Nature 296:39–42 (1982)), the tetracycline (Tet) promoter (Gossen et al., Proc. Nat. Acad. Sci. USA 89:5547–5551 (1995)); prokaryotic expression vectors such as the β-lactamase promoter (Villa-Kamaroff et al., Proc. Natl. Acad. Sci. USA 75:3727–3731 (1978)), or the tac promoter (DeBoer et al., Proc. Natl. Acad. Sci. USA 80:21–25 (1983)); see also "Useful proteins from recombinant bacteria" in Scientific American 242:74–94 (1980); plant expression vectors comprising the nopaline synthetase promoter region (Herrera-Estrella et al., Nature 303:209–213 (1983)) or the cauliflower mosaic virus 35S RNA promoter (Gardner et al., Nucl. Acids Res. 9:2871 (1981)), and the promoter of the photosynthetic enzyme ribulose biphosphate carboxylase (Herrera-Estrella et al., Nature 310:115–120 (1984)); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., Cell 38:639–646 (1984); Ornitz et al., Cold Spring Harbor Symp. Quant. Biol. 50:399–409 (1986); MacDonald, Hepatology 7:425–515 (1987)); insulin gene control region which is active in pancreatic beta cells (Hanahan, Nature 315:115–122 (1985)), immunoglobulin gene control region which is active in lymphoid cells (Grosschedl et al., Cell 38:647–658 (1984); Adames et al., Nature 318:533–538 (1985); Alexander et al., Mol. Cell. Biol. 7:1436–1444 (1987)), mouse mammary tumor virus control region which is active in testicular, breast, lymphoid and mast cells (Leder et al., Cell 45:485–495 (1986)), albumin gene control region which is active in liver (Pinkert et al., Genes Dev. 1:268–276 (1987)), α-fetoprotein gene control region which is active in liver (Krumlauf et al., Mol. Cell. Biol. 5:1639–1648 (1985); Hammer et al., Science 235:3–58 (1987)); α 1-antitrypsin gene control region which is active in the liver (Kelsey et al., Genes Dev. 1: 161–171 (1987)), beta-globin gene control region which is active in myeloid cells (Mogram et al., Nature 315:338–340 (1985); Kollias et al., Cell 46:89–94 (1986)); myelin basic protein gene control region which is active in oligodendrocyte cells in the brain (Readhead et al., Cell 48:703–712 (1987)); myosin light chain-2 gene control region which is active in skeletal muscle (Sani, Nature 314:283–286 (1985)); neuronal-specific enolase (NSE) which is active in neuronal cells (Morelli et al., Gen. Virol. 80:571–83 (1999)); brain-derived neurotrophic factor (BDNF) gene control region which is active in neuronal cells (Tabuchi et al., Biochem. Biophys. Res. Commun. 253:818–823 (1998)); glial fibrillary acidic protein (GFAP) promoter which is active in astrocytes (Gomes et al., Braz. J. Med. Biol. Res. 32:619–631 (1999); Morelli et al., Gen. Virol. 80:571–83 (1999)) and gonadotropic releasing hormone gene control region which is active in the hypothalamus (Mason et al., Science 234:1372–1378 (1986)).

In a specific embodiment, the expression of a Fc-fusion protein is regulated by a constitutive promoter. In another embodiment, the expression of a Fc-fusion protein is regulated by an inducible promoter. In accordance with these embodiments, the promoter may be a tissue-specific promoter. In a specific embodiment, a vector is used that comprises a promoter operably linked to a Fc-fusion protein-encoding nucleic acid, one or more origins of replication, and, optionally, one or more selectable markers (e.g., an antibiotic resistance gene).

In mammalian host cells, a number of viral-based expression systems may be utilized. In cases where an adenovirus is used as an expression vector, the fusion protein coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the Fc-fusion protein molecule in infected hosts (e.g., see Logan & Shenk, Proc. Natl. Acad. Sci. USA 81:355–359 (1984)). Specific initiation signals may also be required for efficient translation of inserted fusion protein coding sequences. These signals include the ATG initiation codon and adjacent sequences.

Furthermore, the initiation codon must be in phase with the reading frame of the desired coding sequence to ensure translation of the entire insert. These exogenous translational control signals and initiation codons can be of a variety of origins, both natural and synthetic.

The efficiency of expression may be enhanced by the inclusion of appropriate transcription enhancer elements, transcription terminators, etc. (see Bitter et al., Methods Enzymol. 153:516–544 (1987)).

Expression vectors containing inserts of a gene encoding a fusion protein can be identified by three general approaches: (a) nucleic acid hybridization, (b) presence or absence of "marker" gene functions, and (c) expression of inserted sequences. In the first approach, the presence of a gene encoding a fusion protein in an expression vector can be detected by nucleic acid hybridization using probes comprising sequences that are homologous to an inserted gene encoding the fusion protein. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding a fusion protein in the vector. For example, if the nucleotide sequence encoding the fusion protein is inserted within the marker gene sequence of the vector, recombinants containing the gene encoding the fusion protein insert can be identified by the absence of the marker gene function. In the third approach, recombinant expression vectors can be identified by assaying the gene product (i.e., fusion protein) expressed by the recombinant. Such assays can be based, for example, on the physical or functional properties of the fusion protein in in vitro assay systems, e.g., binding with anti-bioactive molecule antibody.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled.

Furthermore, different host cells have characteristic and specific mechanisms for the translational and post-translational processing and modification (e.g., glycosylation or phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells, which possess the cellular machinery for proper processing of the primary transcript, glycosylation, and phosphorylation of the gene product, may be used. Such mammalian host cells include but are not limited to CHO, VERY, BHK, HeLa, COS, MDCK, 293, 3T3, WI38, and in particular, neuronal cell lines such as, for example, SK-N-AS, SK-N-FI, SK-N-DZ human neuroblastomas (Sugimoto et al., J. Natl. Cancer Inst. 73:51–57 (1984)), SK-N-SH human neuroblastoma (Biochim. Biophys. Acta 704:450–460 (1982)), Daoy human cerebellar medulloblastoma (He et al., Cancer Res. 52:1144–1148 (1992)), DBTRG-05MG glioblastoma cells (Kruse et al., In Vitro Cell. Dev. Biol. 28A:609–614 (1992)), IMR-32 human neuroblastoma (Cancer Res. 30:2110–2118 (1970)), 1321N1 human astrocytoma (Proc. Natl Acad. Sci. USA 74:4816 (1997)), MOG-G-CCM human astrocytoma (Br. J. Cancer 49:269 (1984)), U87MG human glioblastoma-astrocytoma (Acta Pathol. Microbiol. Scand. 74:465–486 (1968)), A172 human glioblastoma (Olopade et al., Cancer Res. 52:2523–2529 (1992)), C6 rat glioma cells (Benda et al., Science 161:370–371 (1968)), Neuro-2a mouse neuroblastoma (Proc. Natl. Acad. Sci. USA 65:129–136 (1970)), NB41A3 mouse neuroblastoma (Proc. Natl. Acad. Sci. USA 48:1184–1190 (1962)), SCP sheep choroid plexus (Bolin et al., J. Virol. Methods 48:211–221 (1994)), G355–5, PG-4 cat normal astrocyte (Haapala et al., J. Virol. 53:27–833 (1985)), Mpf ferret brain (Trowbridge et al., In Vitro 18:52–960 (1982)), and normal cell lines such as, for example, CTX TNA2 rat normal cortex brain (Radany et al., Proc. Natl. Acad. Sci. USA 89:6467–6471 (1992)), CRL7030 and Hs578Bst. Furthermore, different vector/host expression systems may effect processing reactions to different degrees.

For long-term, high-yield production of recombinant proteins, stable expression is preferred. For example, cell lines that stably express the Fc-fusion protein may be engineered. Rather than using expression vectors that contain viral origins of replication, host cells can be transformed with DNA controlled by appropriate expression control elements (e.g., promoter or enhancer sequences, transcription terminators, polyadenylation sites, etc.), and a selectable marker. Following the introduction of the foreign DNA, engineered cells may be allowed to grow for 1–2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express the differentially expressed or pathway gene protein. Such engineered cell lines may be particularly useful in screening and evaluation of compounds that affect the endogenous activity of the differentially expressed or pathway gene protein.

A number of selection systems may be used, including but not limited to: the herpes simplex virus thymidine kinase (Wigler et al., Cell 11:223 (1997)), hypoxanthine-guanine phosphoribosyltransferase (Szybalska & Szybalski, Proc. Natl. Acad. Sci. USA 48:2026 (1962)), and adenine phosphoribosyltransferase (Lowy et al., Cell 22:817 (1980)) genes can be employed in tk-, hgprt- or aprt-cells, respectively. Also, antimetabolite resistance can be used as the basis of selection for dhfr, which confers resistance to methotrexate (Wigler et al., Proc. Natl. Acad. Sci. USA 77:3567 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Colberre-Garapin et al., J. Mol. Biol. 150:1 (1981)); and hygro, which confers resistance to hygromycin (Santerre et al., Gene 30:147 (1984)) genes.

Purification

The expression of a modified Fc-fusion protein is confirmed by gel electrophoresis using SDS-PAGE reducing or non-reducing protein gel analysis, or any other techniques known in the art. ELISA can also be used to detect both the expression of a modified Fc-fusion protein and the quantity of that Fc-fusion protein.

The modified Fc-fusion proteins described herein may be produced intracellularly, in the periplasmic space, or directly secreted into the medium. Preferably, the modified Fc-fusion proteins in the present invention are secreted into culture media. The media of the host cell culture producing modified Fc-fusion proteins are collected and cell debris is spun down by centrifugation. The supernatants are collected and subjected to the protein expression assays (see more details in the Examples).

Once a Fc-fusion protein of the invention has been produced by recombinant expression, it may be purified using the techniques known in the art, including, but not limited to, filtration and chromatography (e.g., affinity chromatography by protein A, cation exchange chromatography, anion exchange chromatography, and gel filtration), centrifugation, differential solubility, or by any other standard technique for the purification of proteins. The minimum acceptable purity of the Fc-fusion protein for use in pharmaceutical formulation will be 90%, with 95% preferred, 98% more preferred and 99% or higher the most preferred.

Binding Assays for Fc-Fusion Proteins

The binding affinities of the produced Fc-fusion proteins for FcRn can be detected by performing a competitive binding assay at pH 6.0, the optimal condition for binding to FcRn. The binding affinities can be tested by immobilizing FcRn on a solid substrate such as a Sepharose® bead. Alternatively, the binding affinities can be evaluated using an ELISA. Preferably, the present invention tests the binding affinities by carrying out a competitive binding assay in a cell-based system. A dilution series of a produced modified Fc-fusion protein and the unmodified Fc-fusion protein are compared for binding to FcRn expressed on a cell line, preferably an NS0 cell line. The experimental procedures for carrying out a competitive binding assay are described in detail in the Examples below.

The experiments in the present invention show that similar binding affinity results can be achieved with purified Fc-fusion proteins or culture supernatants of the cells producing Fc-fusion proteins. Accordingly, supernatants can be used directly to test the binding affinities for FcRn of the produced Fc-fusion proteins in order to confirm that the desired alteration of the binding affinities has been accomplished. After such a confirmation, the produced Fc-fusion is subjected to more complex purification procedures.

Direct binding assays should also be performed to confirm that the modified Fc-fusion proteins bind to the FcRn in a pH-dependent manner. In particular, the binding affinity of the modified Fc-fusion proteins for FcRn is tested both at pH 6.0 and at pH 8.0 (see more details in Examples). In general, the binding affinity of the modified Fc-fusion proteins at pH 6.0 should exceed that at pH 8.0.

Biological stability (or serum half-life) may be measured by a variety of in vitro or in vivo means. For example, by using a radiolabeled protein and measuring levels of serum radioactivity as a function of time, or by assaying the levels of intact Fc-fusion protein (of known specificity) present in the serum using ELISA as a function of time, with a particularly preferred measure of increased biological stability being evidenced by increased serum half-life and decreased clearance rates. Assay methods for measuring in vivo pharmacokinetic parameters (e.g. in vivo mean elimination half-life) are described in the Examples below, as well as in U.S. patent application Ser. No. 10/687,118, filed Oct. 15, 2003, which is hereby incorporated by reference herein. Modified Fc-fusion proteins of the present invention preferably exhibit an in vivo elimination half-life at least about 1.3-fold longer than that of its corresponding unmodified Fc-fusion protein, and more preferably, the modified Fc-fusion protein has an in vivo elimination half-life at least about 1.5-fold, 1.8-fold, 1.9-fold, or greater than 2.0-fold longer than that of the corresponding unmodified Fc-fusion protein. In alternative embodiments, the amino acid modifications of the present invention may also be used to reduce the serum half-life of a therapeutic or diagnostic Fc-fusion protein.

III. Uses of Modified IgG Fc-Fusion Proteins with Altered FcRn Binding Affinity and/or Serum Half-Lives The methods of making modified Fc-fusion proteins described above may be used in the generation of a series of therapeutic compounds with improved biological stability. Such compounds include, for example, interleukin-2, insulin, interleukin-4, and interferon gamma, or even T cell receptors. The recombinant Fc domains of this invention are also contemplated to be of use in stabilizing a wide range of drugs, which would likely alleviate the need for their repeated administration. However, the present methods are not limited solely to the production of proteins for human administration, and may be employed to produce large quantities of any protein with increased stability, such as may be used, for example, in immunization protocols, in animal treatment by veterinarians, or in rodent in vivo therapy models.

The modified Fc-fusion proteins have various therapeutic applications. The modified Fc-fusion proteins may be used to treat a patient suffering from, or predisposed to, a disease or disorder, who could benefit from administration of the modified Fc-fusion proteins. The conditions that can be treated with the Fc-fusion proteins include cancer; inflammatory conditions such as asthma, autoimmune diseases and viral infections, etc.

The cancers that can be treated by the Fc-fusion proteins described herein include, but are not limited to, breast cancer, squamous cell cancer, small cell lung cancer, non-small cell lung cancer, gastrointestinal cancer, pancreatic cancer, glioblastoma, cervical cancer, ovarian cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma, and various types of head and neck cancer.

The autoimmune diseases include, but are not limited to, Addison's disease, autoimmune diseases of the ear, autoimmune diseases of the eye such as uveitis, autoimmune hepatitis, Crohn's disease, diabetes (Type I), epididymitis, glomerulonephritis, Graves' disease, Guillain-Barre syndrome, Hashimoto's disease, hemolytic anemia, systemic lupus erythematosus, multiple sclerosis, myasthenia gravis, pemphigus vulgaris, psoriasis, rheumatoid arthritis, sarcoidosis, scleroderma, Sjogren's syndrome, spondyloarthropathies, thyroiditis, ulcerative colitis, and vasculitis.

The modified Fc-fusion proteins with reduced serum half-lives in the present invention may be used in the treatment of diseases or disorders where destruction or elimination of tissue or foreign microorganisms is desired. For example, the Fc-fusion protein may be used to treat cancer, inflammatory disorders, infections and other conditions where removal of tissue is desired. The Fc-fusion protein would be generally useful in that the quicker biological clearance times would result in reduced immunogenicity of any protein administered. Other applications would include antibody-based or Fc-fusion protein-based imaging regimens, Fc-fusion protein-based or antibody-based drug removal, or creation of immunotoxins with a shorter half-life.

The modified IgG Fc-fusion protein with increased serum half-lives may be an anti-tissue factor (TF) Fc-fusion protein, anti-IgE Fc-fusion protein, and anti-integrin Fc-fusion protein. The desired mechanism of action may be to block ligand-receptor binding pairs. The modified Fc-fusion proteins with increased serum half-lives may also be agonist Fc-fusion proteins. The Fc-fusion proteins can also be used as therapeutic agents such as vaccines. The dosage and frequency of immunization of such vaccines will be reduced due to the extended serum half-lives of the Fc-fusion proteins.

The modified Fc-fusion proteins of the invention may be formulated in pharmaceutical compositions. Thus, the present invention also provides methods and compositions for administering a therapeutically effective dose of a modified Fc-fusion protein. The exact dose will depend on the purpose of the treatment, and will be ascertainable by one of ordinary skill in the art using well-known techniques (see e.g., Ansel et al., "Pharmaceutical Dosage Forms and Drug Delivery," ($6^{th}$ Ed., Media, Pa.: Williams & Wilkins, 1995); "Pharmaceutical Dosage Forms" (Vols. 1–3, ISBN nos. 0824785762, 082476918X, 0824712692, 0824716981) eds. Lieberman et al. (New York: Marcel Dekker, Inc., 1992); Loyd V. Allen, Jr., "The Art, Science and Technology of Pharmaceutical Compounding," (American Pharmaceutical Association, 1999); and Gloria Pickar, "Dosage Calculations," (Delmar Learning, 1999)). As is well known in the art, adjustments for physiological degradation, systemic versus localized delivery, and rate of new protease synthesis, as well as the age, body weight, general health, sex, diet, time of administration, drug interaction and the severity of the condition may be necessary, and will be ascertainable with routine experimentation by those of ordinary skill in the art.

The pharmaceutical formulations may be administered in a variety of unit dosage forms depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The formulations for administration will commonly comprise a modified Fc-fusion protein of the invention dissolved in a pharmaceutically acceptable carrier or excipient, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (see e.g., "Remington's Pharmaceutical Science," (15th ed., Mack Publ. Co., Easton Pa., 1980); and Goodman & Gillman, "The Pharmacologial Basis of Therapeutics," (Hardman et al., eds., The McGraw-Hill Companies, Inc., 1996)).

The pharmaceutical formulations provided herein may also contain more than one active ingredient as necessary for the particular indication being treated, preferably those with complementary activities that do not adversely affect each other. Such molecules are suitably present in combination in amounts that are effective for the purpose intended.

Active ingredients of the above pharmaceutical formulation may be entrapped in microcapsules, in colloidal drug delivery systems (for example, liposome, albumin microspheres, microemulsions, nano-particles and nanocapsules), in macroemulsions, or in sustained-release preparation. Such techniques are known to people skilled in the art (see, e.g., "Remington's Pharmaceutical Science" (15th ed., Mack Publ. Co., Easton Pa., 1980)).

The present invention provides for pharmaceutical compositions comprising the modified IgG Fc-fusion protein described herein and a pharmaceutically acceptable carrier. The compositions for parenteral administration commonly comprise a solution of the IgG Fc-fusion protein or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. The compositions can contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate. The concentration of the Fc-fusion proteins in these formulations can vary widely, i.e., from less than about 0.01%, usually at least about 0.1% to as much as 5% by weight, and are selected primarily based on fluid volumes and viscosities in accordance with the particular mode of administration selected. A typical composition for intravenous infusion can be made up to contain 250 ml of sterile Ringer's solution, and 10 mg to 100 mg of IgG Fc-fusion protein (see "Remington's Pharmaceutical Science", 15$^{th}$ ed., Mack Publishing Company, Easton, Pa. (1980)).

The pharmaceutical compositions comprising the present Fc-fusion proteins may administered by any suitable means, including parenteral subcutaneous, intraperitoneal, intrapulmonary, and intranasal, and if desired for local immunosuppressive treatment, intralesional administration. Parenteral infusions include intramuscular, intravenous, intraarterial, intraperitoneal, or subcutaneous administration. In addition, the Fc-fusion proteins are suitably administered by pulse infusion, particularly with declining doses of Fc-fusion proteins.

The compositions containing the present Fc-fusion proteins or a cocktail thereof can be administered for prophylactic and/or therapeutic treatments. In therapeutic application, compositions are administered to a patient already affected by the particular disease, in an amount sufficient to cure or at least partially arrest the condition and its complications. An amount adequate to accomplish this is defined as a "therapeutically effective dose." Amounts effective for this use will depend upon the severity of the condition and the general state of the patient's own immune system, but generally range from about 0.01 to about 100 mg of modified Fc-fusion protein per dose, with dosages of 1 to 10 mg per patient being more commonly used.

In prophylactic applications, compositions containing the modified Fc-fusion proteins or a cocktail thereof are administered to a patient not already in a disease state to enhance the patient's resistance. Such an amount is defined to be a "prophylactically effective dose." In this use, the precise amounts again depend upon the patient's state of health and general level of immunity, but generally range from 0.1 to 100 mg per dose, especially dosages of 1 to 10 mg per patient.

Single or multiple administrations of the compositions can be carried out with dose levels and pattern being selected by the treating physician. In any event, the pharmaceutical formulations should provide a quantity of the mutant Fc-fusion proteins of this invention sufficient to effectively treat the patient.

The modified Fc-fusion proteins of the present invention also may be used for various non-therapeutic purposes. They may be used as an affinity purification agent. They may also be useful in diagnostic assays, such as detecting expression of an antigen of interest in specific cells, tissues, or serum. For diagnostic applications, the Fc-fusion proteins typically will be labeled with a detectable moiety, including radioisotopes, fluorescent labels, and various enzyme substrate labels. The Fc-fusion proteins may also be employed in any known assay method, such as competitive binding assays, direct and indirect sandwich assays, and immunoprecipitation assays. The Fc-fusion proteins may also be used for in vivo diagnostic assays. Generally, the Fc-fusion proteins are labeled with a radionucleotide so that the antigen or cell expressing it can be localized using immunoscintigraphy.

Kits can also be supplied for use with the modified Fc-fusion proteins in the protection against or detection of a cellular activity or for the presence of a selected cell surface receptor or the diagnosis of disease. Thus, the subject composition of the present invention may be provided, usually in a lyophilized form in a container, either alone or in conjunction with additional Fc-fusion proteins specific for the desired cell type. The modified Fc-fusion proteins, which may be conjugated to a label or toxin, or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of active IgG Fc-fusion protein, and usually present in total amount of at least about 0.001% wt. based again on the IgG Fc-fusion protein concentration. Frequently, it will be desirable to include an inert extender or excipient to dilute the active ingredients, where the excipient may be present in from about 1 to 99% wt. of the total composition. Where a second antibody capable of binding to the modified IgG Fc-fusion protein is employed in an assay, this will usually be present in a separate vial. The second antibody is typically conjugated to a label and formulated in an analogous manner with the IgG Fc-fusion protein formulations described above.

Each reference cited herein are expressly incorporated by reference herein in its entirety. The following examples are offered by way of illustration and not by way of limitation.

EXAMPLES

Example 1

This example describes the Fc-fusion expression vectors used in the present invention.

The components of the Fc-fusion expression plasmid pMJ001, a derivative of pVk.rg (Cole et al., J. Immunol. 159:3613–3621 (1997)), are as follows. As shown in FIG. 1, proceeding clockwise from the EcoRI site, the receptor/Fc-fusion unit begins with the human cytomegalovirus (hCMV) major immediate early (IE) promoter and enhancer (Boshart et al., Cell 41:521–530 (1985)) as an EcoRI-XbaI fragment. The hCMV region is followed by an XbaI-PinAI fragment comprised of the M195 signal sequence (Co et al., J. Immunol. 148:1149–1154 (1992)) joined to the extracellular domains of the human tumor necrosis factor receptor II (TNF-RII) (Smith et al., Science 248:1019–1023 (1990)). The TNF-RII region is fused in-frame, via a flexible linker region, to a modified genomic DNA fragment containing a portion of the human gamma-1 heavy chain constant region (Ellison et al., Nucleic Acids Res. 10:4071–4079 (1982)) as a PinAI-SphI fragment, including the hinge (H), $C_H2$, and $C_H3$ exons with the intervening introns, and a polyadenylation (polyA) signal for mRNA processing following $C_H3$.

The TNF-RII/Fc-fusion gene is followed by a gene encoding xanthine guanine phosphoribosyl transferase (gpt), together with regulatory elements from SV40 needed for transcription, which was taken as an SphI-EcoRI fragment from the plasmid pvk.rg (Cole et al., op. cit.). The function of the gpt gene is to provide a selectable drug-resistance marker after transfection of the plasmid into mammalian cells. The SphI-EcoRI fragment also contains part of the plasmid pBR322 (Sutcliffe, Cold Spring Harbor Symp. Quant. Biol. 43:77–90 (1979)) comprising the bacterial origin of replication and ampicillin resistance gene for selection in *E. coli*.

Figure 2:
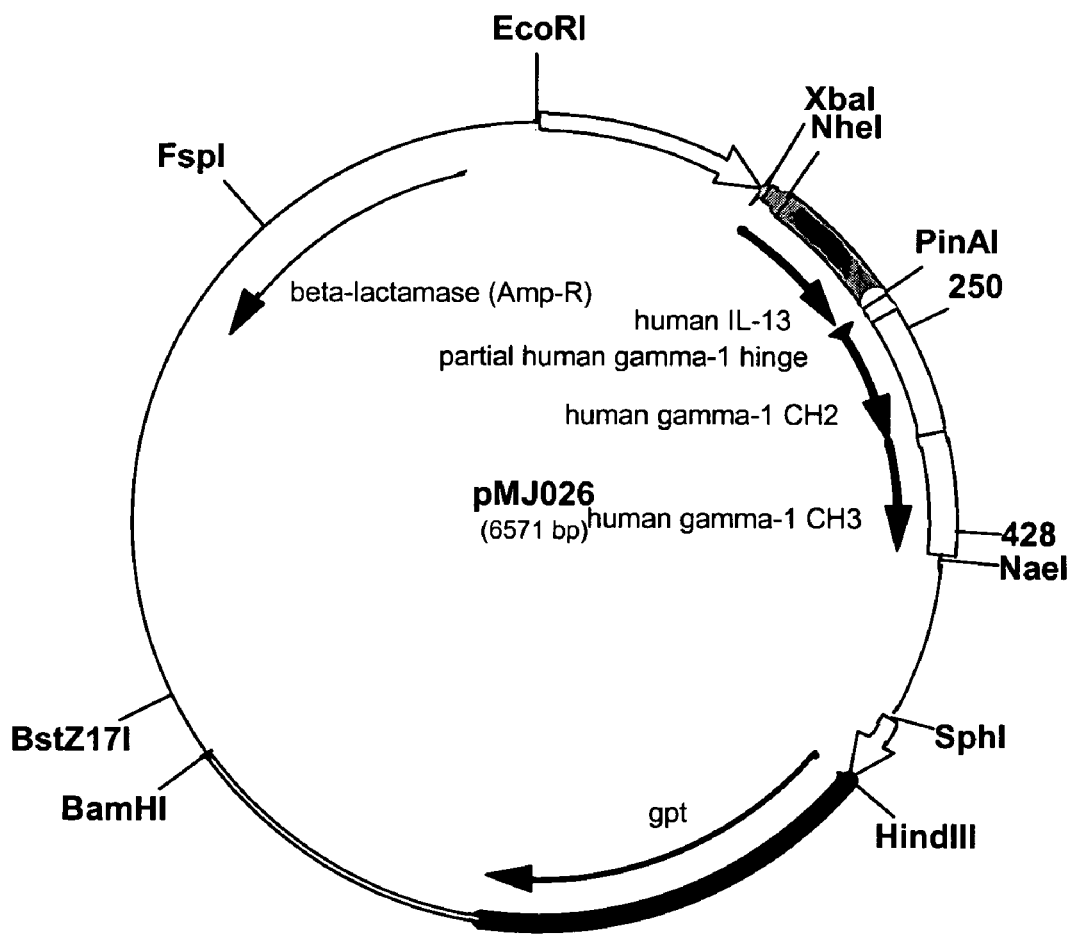

The components of the Fc-fusion expression plasmid pMJ026 (see FIG. 2), a derivative of pvk.rg (Cole et al., op. cit.), are identical to those described above for the expression plasmid pMJ001, with two exceptions. First, the XbaI-PinAI fragment of pMJ026 is comprised of the M195 signal sequence (Co et al., op. cit.) joined to the human interleukin-13 (IL-13) gene (Minty et al., Nature 362:248–250). Second, the IL-13 region is fused in-frame, via a flexible linker region, to a modified cDNA fragment containing a portion of the human gamma-1 heavy chain constant region (Ellison et al., op. cit.) as a PinAI-NaeI fragment, including the 10 carboxy-terminal amino acids of the hinge (H), and the $C_H2$ and $C_H3$ exons without the intervening introns.

Figure 3:
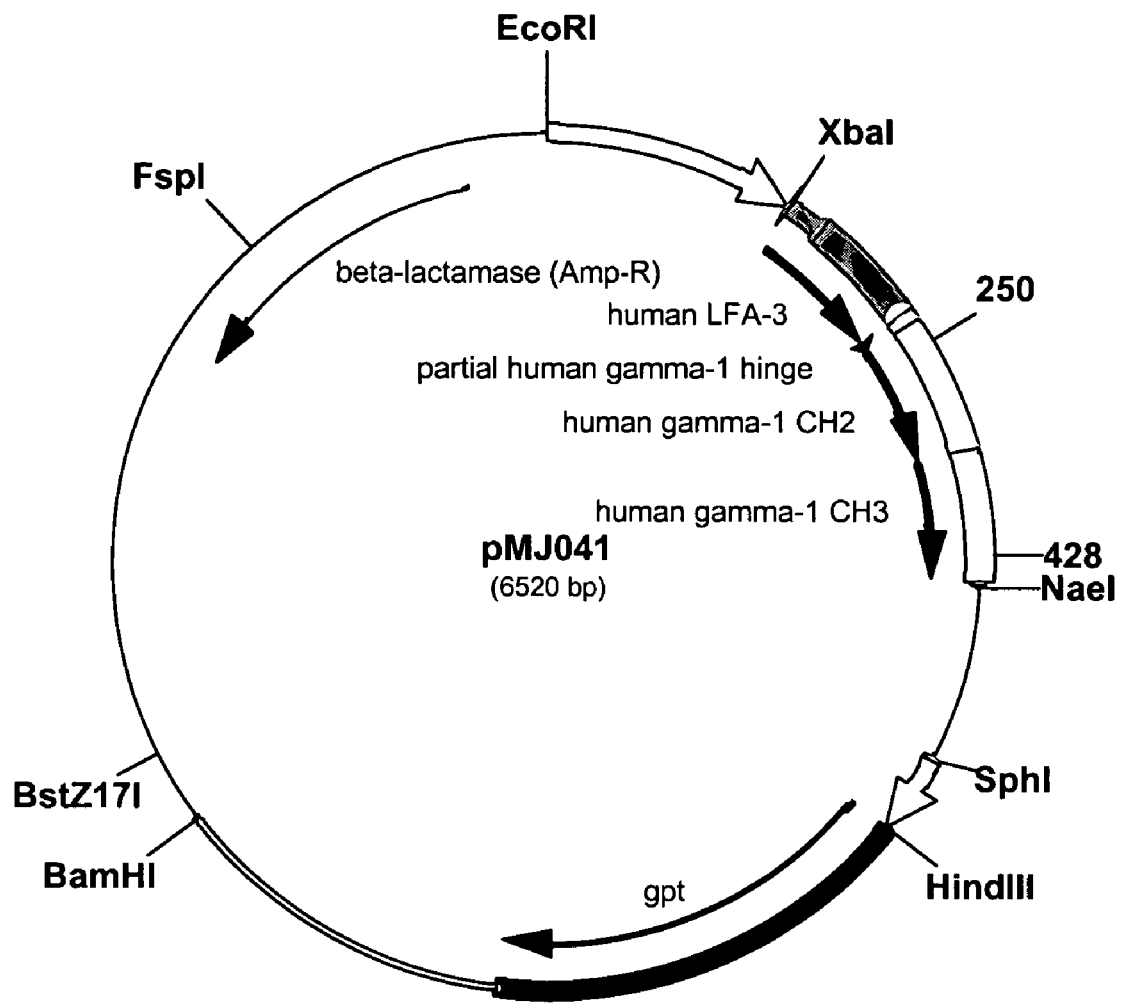

The components of the Fc-fusion expression plasmid pMJ041 (see FIG. 3), a derivative of pvk.rg (Cole et al., op. cit.), are identical to those described above for the expression plasmid pMJ026, with the following modification. The XbaI-NaeI fragment of pMJ041 is comprised of the CD2 binding portion of the human lymphocyte function associated antigen 3 (LFA-3) gene (Wallner et al., J. Exp. Med. 166:923–932 (1987)) preceded by its signal sequence, fused in-frame to the same modified cDNA fragment comprising a portion of the human gamma-1 heavy chain constant region (Ellison et al., op. cit.) as described above for pMJ026.

Example 2

This example describes the construction and mutagenesis of the TNF-RII/Fc-fusion plasmid used in the present invention.

Plasmid Construction:

Human TNF-RII was cloned by PCR from a cDNA library prepared from human peripheral blood mononuclear cells. The extracellular domains of the human TNF-RII gene were modified by PCR to add a flanking NheI site and the C-terminal portion of the M195 heavy chain signal peptide (Co et al., op. cit.) at the 5' end, and a flanking PinAI site at the 3' end. The genomic human gamma-1 heavy chain constant region was modified by PCR to add a flanking PinAI site at the 5' end and a synthetic dipeptide linker consisting of the sequence Gly-Gly fused to the hinge, and an SphI site at the 3' end. The expression vector pMJ001 (see FIG. 1), a derivative of pvk.rg (Cole et al., op. cit.), was constructed by replacing the XbaI-SphI fragment containing the genomic human kappa constant region with an XbaI-SphI fragment comprised of an XbaI-NheI fragment containing the N-terminal portion of the M195 heavy chain signal sequence (Co et al., op. cit.), an NheI-PinAI fragment encoding the C-terminal portion of the M195 heavy chain signal sequence joined to the extracellular domains of human TNF-RII (Smith et al., op. cit.), and a PinAI-SphI fragment containing the hinge-Fc portion of the genomic human immunoglobulin gamma-1 gene (Ellison et al., op. cit.).

Mutagenesis:

The overlap-extension PCR method (Higuchi, in "PCR Technology: Principles and Applications for DNA Amplification", Stockton Press, New York, pp. 61–70 (1989)) was used to generate amino acid substitutions at positions 250 and 428 of the IgG1 heavy chain Fc region (numbered according to the EU index of Kabat et al., op. cit.) in the TNF-RII/Fc-fusion expression vector. To generate the T250Q mutant, the mutagenesis primers JXT250Q1 (5'-AAC CCA AGG ACC AAC TCA TGA TCT CCC G-3') (SEQ ID NO: 58) and JXT250Q2 (5'-GGA GAT CAT GAG TTG GTC CTT GGG TTT TG-3') (SEQ ID NO: 59) were used to modify the Fc region of plasmid pMJ001. The first round of PCR used outside primer MJ-13 (5'-GTC CAC ACG ATC CCA ACA CAC GCA G-3') (SEQ ID NO: 60) and JXT250Q2 for the left-hand fragment, and outside primer MJ-14 (5'-TAT AGA GAT CTG GCG CAC TAA AAA C-3') (SEQ ID NO: 61) and JXT250Q1 for the right-hand fragment. The PCR reactions were done using the Expand™ High Fidelity PCR System (Roche Diagnostics Corporation, Indianapolis, Ind.) by incubating at 94° C. for 2 minutes, followed by 25 cycles of 94° C. for 20 seconds, 55° C. for 20 seconds and 72° C. for 60 seconds, followed by incubating at 72° C. for 7 minutes. The PCR products were run on a low-melting point agarose gel, excised from the gel, and melted at 70° C. The second round of PCR to combine the left-hand and right-hand fragments was done as described above, using outside primers MJ-13 and MJ-14, by incubating at 94° C. for 2 minutes, followed by 35 cycles of 94° C. for 20 seconds, 55° C. for 20 seconds and 72° C. for 90 seconds, followed by incubating at 72° C. for 7 minutes. The final PCR products were run on a low-melting point agarose gel and DNA fragments of the expected size were excised and purified using the QIAquick™ Gel Extraction Kit (QIAGEN®, Valencia, Calif.). The purified fragments were digested with PinAI and SphI, gel-purified as described above, and cloned between the corresponding sites in pMJ001.

To generate the M428L mutant, the mutagenesis primers JXM428L1 (5'-CTC ATG CTC CGT GTT GCA TGA GGC TCT GC-3') (SEQ ID NO: 62) and JXM428L2 (5'-AGA GCC TCA TGC AAC ACG GAG CAT GAG-3') (SEQ ID NO: 63) were used to mutagenize the Fc region of an intermediate plasmid derived from pVg1 (Co et al., op. cit.). The first round of PCR used outside primer JX080 (5'-CCT CAG CTC GGA CAC CTT CTC-3') (SEQ ID NO: 64) and JXM428L2 for the left-hand fragment, and outside primer NT244 (5'-GCC TCC CTC ATG CCA CTC A-3') (SEQ ID NO: 65) and JXM428L1 for the right-hand fragment. The second round of PCR to combine the left-hand and right-hand fragments was done using outside primers JX080 and NT244, as described above. The final PCR products were gel-purified, digested with NheI and EagI, and subcloned into the intermediate plasmid. The BsrGI restriction fragment, which contains the M428L mutation, was excised from the intermediate plasmid, gel-purified, and cloned between the corresponding sites in pMJ001.

To generate the T250Q/M428L double mutant, the BsrGI restriction fragment of the pMJ001 plasmid variant containing the T250Q mutation was replaced with the corresponding fragment from the intermediate plasmid containing the M428L mutation, as described above.

Plasmid DNA was prepared using the QIAprep™ Spin Miniprep Kit (QIAGEN®), and nucleotide substitutions were confirmed by sequencing. Large-scale plasmid DNA preparations were made using the EndoFree™ Plasmid Maxi Kit (QIAGEN®). The coding regions of the TNF-RII/Fc-fusion expression plasmids were verified by nucleotide sequencing.

Results:

In order to identify human Fc-fusion protein mutants with increased affinity to the neonatal Fc receptor (FcRn), which would be expected to have increased serum half-lives, several amino acid substitutions were generated at positions 250 and 428 (numbered according to the EU index of Kabat et al., op. cit.) of the human γ1 heavy chain Fc region of the TNF-RII/Fc-fusion protein. Although the wild-type amino acids at positions 250 and 428 are located near the Fc/FcRn interface, these residues do not appear to directly contribute to the pH-dependent interaction between Fc and FcRn. Therefore, amino acid substitutions at these positions may increase the affinity of Fc for FcRn while maintaining pH-dependent binding. Thus, in addition to the wild-type TNF-RII/Fc-fusion protein (SEQ ID NO: 66), both single and double mutants were generated, including the single mutant M428L (SEQ ID NO: 67) and the double mutant T250Q/M428L (SEQ ID NO: 68).

Example 3

This example describes the construction and mutagenesis of the IL-13/Fc-fusion expression vector used in the present invention.

Plasmid Construction:

Human IL-13 was cloned by PCR from a cDNA library prepared from human peripheral blood mononuclear cells that were activated with PMA and anti-CD28 antibody. The human IL-13 gene was modified by PCR to add a flanking NheI site and the C-terminal portion of the M195 heavy chain signal peptide (Co et al., op. cit.) at the 5' end, and a flanking PinAI site at the 3' end. The human cDNA gamma-1 heavy chain constant region was modified by PCR to add a flanking PinAI site at the 5' end and a synthetic peptide linker consisting of the sequence Gly-Gly-Ala-Ala fused to a partial hinge, and an NaeI site at the 3' end. The expression vector pMJ026 (see FIG. 2), a derivative of pvk.rg (Cole et al., op. cit.), was constructed by replacing the XbaI-NaeI fragment containing the genomic human kappa constant region with an XbaI-NaeI fragment comprised of an XbaI-NheI fragment containing the N-terminal portion of the M195 heavy chain signal sequence (Co et al., op. cit.), an NheI-PinAI fragment encoding the C-terminal portion of the M195 heavy chain signal sequence joined to human IL-13 (Minty et al., op. cit.), and a PinAI-NaeI fragment containing the partial hinge-Fc portion of the human immunoglobulin gamma-1 cDNA sequence (Ellison et al., op. cit.).

Mutagenesis:

PCR was used to generate amino acid substitutions at positions 250 and 428 of the IgG1 heavy chain Fc region (numbered according to the EU index of Kabat et al., op. cit.) in the IL-13/Fc-fusion expression vector. RNA isolated from cell lines stably expressing either OST577-IgG1 wild-type or double mutant T250Q/M428L (Hinton et al., PCT Publication WO 04/035752) was used to generate first-strand cDNA. The resulting cDNA was used as template in PCR reactions done using the Expand™ High Fidelity PCR System (Roche Diagnostics Corporation) by incubating at 94° C. for 2 minutes, followed by 35 cycles of 94° C. for 20 seconds, 55° C. for 20 seconds and 72° C. for 60 seconds, followed by incubating at 72° C. for 7 minutes. The PCR reactions were done using outside primers MJ-24 (5'-ACT ACC GGT GGG GGG GCT GCA GAC AAA ACT CAC ACA-3') (SEQ ID NO: 69) and MC124 (5'-GCA CCC AGC GCT GCC CT-3') (SEQ ID NO: 70). The PCR products were run on a low-melting point agarose gel and DNA fragments of the expected size were excised and purified using the QIAquick™ Gel Extraction Kit (QIAGEN®). The purified fragments were digested with PinAI and NaeI, gel-purified as described above, and cloned between the corresponding sites in pMJ026.

Plasmid DNA was prepared using the QIAprep™ Spin Miniprep Kit (QIAGEN®), and nucleotide substitutions were confirmed by sequencing. Large-scale plasmid DNA preparations were made using the EndoFree™ Plasmid Maxi Kit (QIAGEN®). The coding regions of the IL-13/Fc-fusion expression plasmids were verified by nucleotide sequencing.

Results:

Amino acid substitutions were generated at positions 250 and 428 (numbered according to the EU index of Kabat et al., op. cit.) of the human γ1 heavy chain Fc region of the IL-13/Fc-fusion protein. Although the wild-type amino acids at positions 250 and 428 are located near the Fc/FcRn interface, these residues do not appear to directly contribute to the pH-dependent interaction between Fc and FcRn. Therefore, amino acid substitutions at these positions may increase the affinity of Fc for FcRn while maintaining pH-dependent binding. Thus, in addition to the wild-type IL-13/Fc-fusion protein (SEQ ID NO: 71), a T250Q/M428L double mutant (SEQ ID NO: 72) form was generated for comparison to the wild-type Fc-fusion protein.

Example 4

This example describes the construction and mutagenesis of the LFA-3/Fc-fusion plasmid used in the present invention.

Plasmid Construction:

The CD2 binding portion of human LFA-3, preceded by the LFA-3 signal peptide (Wallner et al., op. cit.), was generated and cloned by GenScript Corporation (Piscataway, N.J.) using GenScript™ technology and was modified to add a flanking XbaI site at the 5' end, and a flanking PinAI site at the 3' end. The human cDNA gamma-1 heavy chain constant region was modified by PCR to add a flanking PinAI site at the 5' end and a synthetic peptide linker consisting of the sequence Gly-Gly-Ala-Ala fused to a partial hinge, and an NaeI site at the 3' end. The expression vector pMJ041, a derivative of pvk.rg (Cole et al., op. cit.), was constructed by replacing the XbaI-NaeI fragment containing the genomic human kappa constant region with an XbaI-NaeI fragment comprised of the LFA-3 signal sequence and CD2 binding gene sequence (Wallner et al., op. cit.) and the partial hinge-Fc portion of the human immunoglobulin gamma-1 cDNA sequence (Ellison et al., op. cit.). First, an intermediate expression vector, derived from pvk.rg (Cole et al., op. cit.), was constructed by replacing the XbaI-NaeI fragment containing the genomic human kappa constant region with an XbaI-NaeI fragment comprised of an XbaI-PinAI fragment containing the LFA-3 signal sequence and the CD2 binding portion of the LFA-3 gene (Wallner et al., op. cit.), and a PinAI-NaeI fragment containing the partial hinge-Fc portion of the human immunoglobulin gamma-1 cDNA sequence (Ellison et al., op. cit.). PCR was then used to remove the PinAI cloning site and the Gly-Gly-Ala-Ala linker. The first round of PCR used outside primer MBR3 (5'-CCA TAG AAG ACA CCG GGA CC-3') (SEQ ID NO: 73) and MJ-59 (5'-GAG TTT TGT CGA CAT AAA GAA AGA AC-3') (SEQ ID NO: 74) for the left-hand fragment, and outside primer MC124 and MJ-60 (5'-TCT TTC TTT ATG TCG ACA AAA CTC ACA CAT GCC-3') (SEQ ID NO: 75) for the right-hand fragment. The PCR reactions, using the above mentioned intermediate vector as template, were done using the Expand™ High Fidelity PCR System (Roche Diagnostics Corporation) by incubating at 94° C. for 2 minutes, followed by 25 cycles of 94° C. for 20 seconds, 55° C. for 20 seconds and 72° C. for 75 seconds, followed by incubating at 72° C. for 7 minutes. The second round of PCR to combine the left-hand and right-hand fragments was done as described above using outside primers MBR3 and MC 124, by incubating 94° C. for 2 minutes, followed by 25 cycles of 94° C. for 20 seconds, 55° C. for 20 seconds and 72° C. for 90 seconds, followed by incubating at 72° C. for 7 minutes. The final PCR products were gel-purified, digested with XbaI and NaeI, and subcloned into the corresponding sites in the intermediate vector, resulting in pMJ041 (see FIG. 3).

Mutagenesis.

PCR was used, as described above for the IL-13/Fc-fusion vectors, to generate amino acid substitutions at positions 250 and 428 of the IgG1 heavy chain Fc region (numbered according to the EU index of Kabat et al., op. cit.) in the LFA-3/Fc-fusion plasmid.

Plasmid DNA was prepared using the QIAprep™ Spin Miniprep Kit (QIAGEN®), and nucleotide substitutions were confirmed by sequencing. Large-scale plasmid DNA preparations were made using the EndoFree™ Plasmid Maxi Kit (QIAGEN®). The coding regions of the LFA-3/Fc-fusion expression plasmids were verified by nucleotide sequencing.

Results:

Amino acid substitutions were generated at positions 250 and 428 (numbered according to the EU index of Kabat et al., op. cit.) of the human γ1 heavy chain Fc region of the LFA-3/Fc-fusion protein. Although the wild-type amino acids at positions 250 and 428 are located near the Fc/FcRn interface, these residues do not appear to directly contribute to the pH-dependent interaction between Fc and FcRn. Therefore, amino acid substitutions at these positions may increase the affinity of Fc for FcRn while maintaining pH-dependent binding. Thus, in addition to the wild-type LFA-3/Fc-fusion protein (SEQ ID NO: 76), a T250Q/M428L double mutant (SEQ ID NO: 77) form was generated for comparison to the wild-type Fc-fusion protein.

Example 5

This example describes the FcRn expression vector used in the present invention.

The base expression vector pDL172, a derivative of pVk.rg (Cole et al., op. cit.), was constructed by replacing the XbaI-SphI fragment containing the genomic human kappa constant region with an XbaI-SphI fragment comprised of an XbaI-NheI fragment containing the N-terminal portion of the M195 heavy chain signal sequence (Co et al., op. cit.), a 0.7 kb NheI-PinAI fragment, a synthetic PinAI-EagI fragment encoding a human c-myc decapeptide, flanked by linker peptides, that is recognized by mouse monoclonal antibody 9E10 (Evan et al., Mol. Cell. Biol. 5:3610–3616 (1985)), followed by the GPI linkage signal from human decay accelerating factor (Caras et al., Nature 325:545–549 (1987)), and an EagI-SphI fragment containing the polyA signal of the human immunoglobulin gamma-1 gene (Ellison et al., op. cit.).

Figure 4:
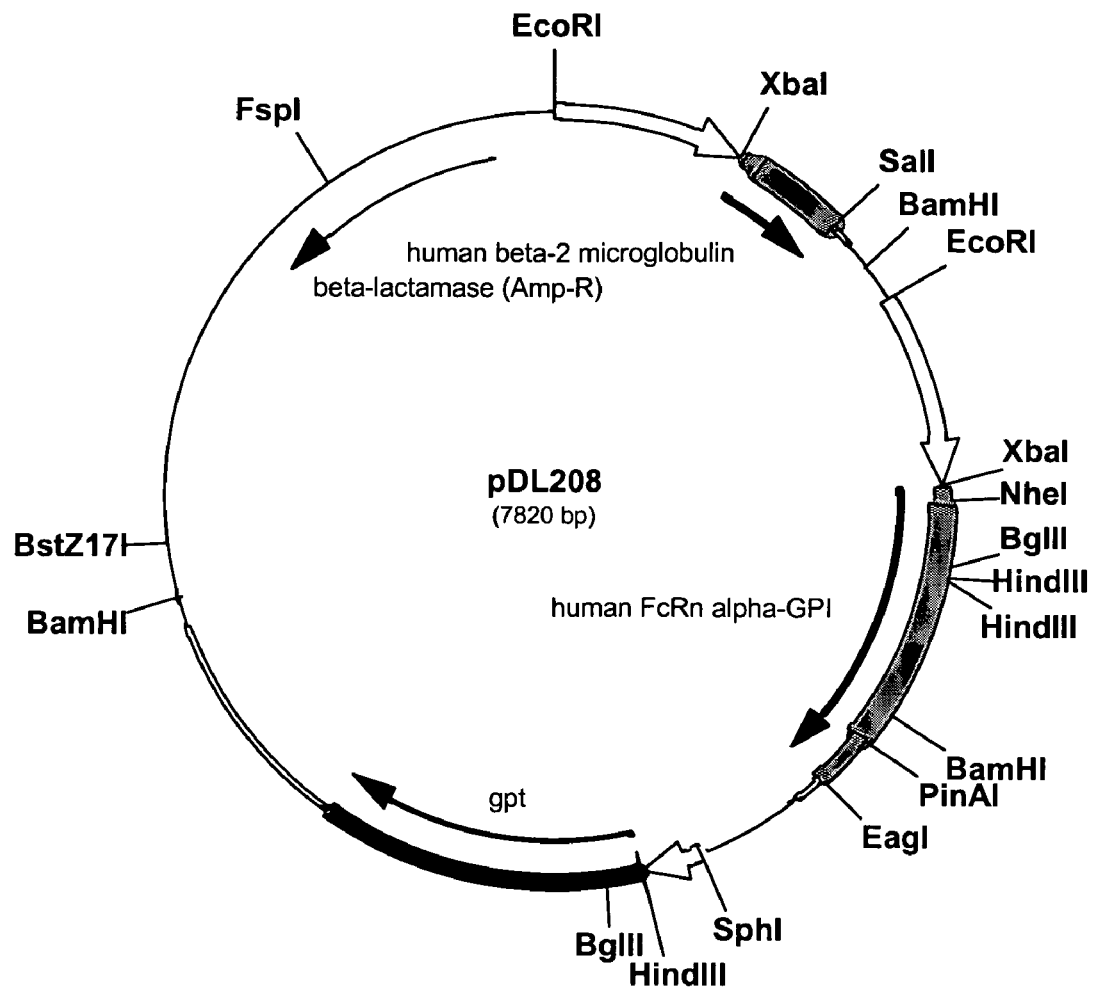

Human beta-2 microglobulin (β2m) and the extracellular domains of the human neonatal Fc receptor (FcRn) alpha chain were cloned by PCR from a cDNA library prepared from human peripheral blood mononuclear cells. The human FcRn alpha chain gene was modified by PCR to add a flanking NheI site and the C-terminal portion of the M195 heavy chain signal sequence at the 5' end, and a flanking PinAI site at the 3' end, and used to replace the NheI-PinAI fragment of pDL172, resulting in expression vector pDL172+HuFcRn. The human β2m gene was modified by PCR to add flanking XbaI and SalI sites at the 5' and 3' ends, respectively, and to remove an internal EcoRI site. The resulting XbaI-SalI fragment was subcloned into an intermediate vector, flanked on its 5' end by an EcoRI-XbaI fragment containing the hCMV IE promoter and enhancer (Boshart et al., op. cit.), and on its 3' end by a SalI-BamHI fragment containing the polyadenylation signal of the murine immunoglobulin gamma-2a gene (Kostelny et al., J Immunol. 148:1547–1553 (1992)), followed by a BamHI-EcoRI fragment containing the transcriptional terminator of the human complement gene C2 (Ashfield et al., EMBO J. 10:4197–4207 (1991)). The resulting EcoRI-EcoRI fragment containing a functional human β2m transcriptional unit was cloned into the unique EcoRI site of pDL172+HuFcRn, resulting in expression vector pDL172+HuFcRn+Huβ2m, hereinafter referred to as pDL208 (see FIG. 4).

Example 6

This example describes the expression and purification of mutant IgG1 Fc-fusion proteins.

Cell Culture:

Human kidney cell line 293-H (Life Technologies®, Rockville, Md.) was maintained in DMEM (BioWhittaker™, Walkersville, Md.) containing 10% Fetal Bovine Serum (FBS) (HyClone, Logan, Utah), 0.1 mM MEM non-essential amino acids (Invitrogen™, Carlsbad, Calif.) and 2 mM L-glutamine (Invitrogen™), hereinafter referred to as 293 medium, at 37° C. in a 7.5% $CO_2$ incubator. For expression and purification of Fc-fusion proteins after transient transfection, 293-H cells were incubated in DMEM (BioWhittaker™) containing 10% low-IgG FBS (HyClone®), 0.1 mM MEM non-essential amino acids (Invitrogen™) and 2 mM L-glutamine (Invitrogen™), hereinafter referred to as low-IgG 293 medium, or Hybridoma-SFM (HSFM) (Life Technologies®).

Mouse myeloma cell line NS0 (European Collection of Animal Cell Cultures, Salisbury, Wiltshire, UK) was maintained in DMEM (BioWhittaker™) containing 10% FBS (HyClone®) at 37° C. in a 7.5% $CO_2$ incubator. For expression and purification of Fc-fusion proteins after stable transfection, NS0 cells were incubated in HSFM (Life Technologies®) with 2% low-IgG FBS (HyClone®).

Transient Transfections:

293-H cells were transiently transfected with plasmid pMJ001, pMJ026, or variants containing mutations in the respective Fc region. For large-scale transient transfections, approximately $7 \times 10^6$ cells per transfection were plated in a T-75 flask in 25 ml of 293 medium and grown overnight to confluence. The next day, 24 μg of wild-type or mutated plasmid were combined with 1.5 ml of HSFM (Life Technologies®). In a separate tube, 60 μl of Lipofectamine™ 2000 (Life Technologies®) reagent and 1.5 ml of HSFM (Life Technologies®) were combined and incubated for 5 minutes at room temperature. The 1.5 ml Lipofectamine™ 2000-HSFM mixture was mixed gently with the 1.5 ml DNA-HSFM mixture and incubated at room temperature for 20 minutes. The medium covering the 293-H cells was aspirated and replaced with low-IgG 293 medium or HSFM (Life Technologies®) containing 2% low-IgG FBS (HyClone®), then the lipofectamine-DNA complexes were added dropwise to the cells, mixed gently by swirling, and the cells were incubated for 5–7 days at 37° C. in a 7.5% $CO_2$ incubator before harvesting the supernatants.

Stable Transfections:

NS0 cells were stably transfected with pMJ026, pMJ041, or variants containing mutations in the respective Fc region. Approximately $1 \times 10^7$ cells were washed once and resuspended in 1 ml of plain DMEM (BioWhittaker™), transferred to a Gene Pulser™ Cuvette (Bio-Rad® Laboratories, Hercules, Calif.), and incubated on ice for 10 minutes. Forty μg of plasmid was linearized with FspI and gently mixed with the cells on ice, then the cells were electroporated by pulsing twice using a Gene Pulser™ II (Bio-Rad® Laboratories) set at 1.5 kV, 3 μF, and returned to ice for 10 minutes. The cells were diluted in 40 ml of DMEM (BioWhittaker™), 10% FBS (HyClone®), and plated in four 96-well plates at 100 μl/well. After 48 hours, 100 μl/well of mycophenolic acid (MPA) selection medium (DMEM (BioWhittaker™), 10% FBS (HyClone®), 1× HT Media Supplement Hybri-Max® (Sigma-Aldrich, St. Louis, Mo.), 250 μg/ml xanthine (Sigma-Aldrich), 1 μg/ml mycophenolic acid (Life Technologies®), and 2 mM L-glutamine (Invitrogen™)) or 2× MPA selection medium was added. Mycophenolic acid-resistant NS0 transfectants from wells apparently containing single colonies were expanded in DMEM (BioWhittaker™) with 10% FBS (HyClone®) and adapted to HSFM (Life Technologies®) containing 2% low-IgG FBS (HyClone®).

Fc-Fusion Purification:

Culture supernatants from transient transfections with pMJ001 and variants were harvested by centrifugation, and sterile filtered. The pH of the filtered supernatants was adjusted by addition of 1/75 volume of 1 M Tris-HCl, pH 8.0. Supernatants were run over a 1 ml HiTrap® Protein G HP column (Amersham Biosciences™ Corporation, Piscataway, N.J.) that was pre-equilibrated with 20 mM sodium phosphate, pH 7.0. The column was washed with the same buffer, and bound Fc-fusion protein was eluted with 100 mM glycine-HCl, pH 2.7. After neutralization by addition of ~1/50 volume of 1 M Tris-HCl, pH 8.0, the pooled protein fractions were run over a 5 ml HiTrap® Desalting column (Amersham Biosciences™ Corporation) that was pre-equilibrated with PBS, pH 6.0. The flow-through was collected and fractions with $OD_{280}$>0.1 were pooled and concentrated to ~0.5–1.0 mg/ml using 2 ml Vivaspin® concentrators (50,000 dalton MWCO) (Vivascience® AG, Hannover, Germany). Samples were then filter sterilized using 0.2 μm Millex®-GV microfilters (Millipore® Corporation, Bedford, Mass.). The concentrations of the purified Fc-fusion proteins were determined by UV spectroscopy by measuring the absorbance at 280 nm (1 mg/ml=1.8 $A_{280}$).

Culture supernatants from transient transfections with pMJ026 and variant were harvested by centrifugation, and sterile filtered. The pH of the filtered supernatants was adjusted by addition of 1/50 volume of 1 M sodium citrate, pH 7.0. Supernatants were run over a 1 ml HiTrap® Protein A HP column (Amersham Biosciences™ Corporation) that was pre-equilibrated with 20 mM sodium citrate, 150 mM NaCl, pH 7.0. The column was washed with the same buffer, and bound Fc-fusion protein was eluted with 20 mM sodium citrate, pH 3.5. After neutralization by addition of 1/50 volume of 1.5 M sodium citrate, pH 6.5, the pooled antibody fractions were run over a 5 ml HiTrap® Desalting column (Amersham Biosciences™ Corporation) that was pre-equilibrated with 20 mM sodium citrate, 120 mM NaCl, pH 6.0. The flow-through was collected and fractions with $OD_{280}$>0.1 were pooled, concentrated to ~0.5–1.0 mg/ml, and filter sterilized, as described above. The concentrations of the purified Fc-fusion proteins were determined by UV spectroscopy by measuring the absorbance at 280 nm (1 mg/ml=2.0 $A_{280}$).

Culture supernatants from stable transfections with pMJ026, pMJ041 or variants containing mutations in the respective Fc region were harvested by centrifugation, and sterile filtered. Supernatants were run over a 1 ml HiTrap® Protein A HP column (Amersham Biosciences™ Corporation) that was pre-equilibrated with PBS supplemented with 500 mM NaCl, pH 7.0. The column was washed with the same buffer followed by PBS and bound Fc-fusion protein was eluted with 50 mM glycine, 250 mM NaCl, pH 3.5. After neutralization by addition of 1/10 volume of 1M HEPES, pH 7.8, the pooled antibody fractions were run over a 5 ml HiTrap® Desalting column (Amersham Biosciences™ Corporation) that was pre-equilibrated with PBS, pH 6.0. The flow-through was collected and fractions with $OD_{280}$>0.1 were pooled, concentrated to ~0.5–1.0 mg/ml, and filter sterilized, as described above. The concentrations of the purified Fc-fusion proteins were determined by UV spectroscopy by measuring the absorbance at 280 nm (1 mg/ml=2.0 $A_{280}$).

SDS-PAGE:

Five μg samples of purified Fc-fusion proteins were run under reducing conditions on NuPAGE® Novex® 4–12% Bis-Tris gels (Invitrogen™) and stained using the SimplyBlue™ SafeStain Kit (Invitrogen™) following the manufacturer's recommendations.

Results:

The wild-type and mutant human gamma-1 Fc regions were expressed as TNF-RII/Fc-fusion proteins, comprising the extracellular domains of human TNF-RII (Smith et al., op. cit.), and the hinge-Fc region of the heavy chain constant regions of human gamma-1 (Ellison et al., op. cit.). As described above, the wild-type or mutant Fc-fusion expression vectors were transiently transfected into 293-H cells for expression of TNF-RII/Fc-fusion proteins, and the expressed proteins were purified by protein G affinity chromatography.

Purified TNF-RII/Fc-fusion proteins were characterized by SDS polyacrylamide gel electrophoresis (SDS-PAGE). SDS-PAGE analysis under reducing conditions indicated that the purified Fc-fusion proteins consisted of a predominant species with a molecular weight of about 70 kD (data not shown).

The wild-type and mutant human gamma-I Fc regions were also expressed as IL-13/Fc-fusion proteins, comprising human IL-13 (Minty et al., op. cit.), and the hinge-Fc region of the heavy chain constant regions of human gamma-I (Ellison et al., op. cit.). As described above, the wild-type or mutant Fc-fusion expression vectors were transiently transfected into 293-H cells or stably transfected into NS0 cells for expression of IL-13/Fc-fusion proteins, and the expressed proteins were purified by protein A affinity chromatography.

Purified IL-13/Fc-fusion proteins were characterized by SDS-PAGE. SDS-PAGE analysis under reducing conditions indicated that the purified Fc-fusion proteins consisted of a predominant species with a molecular weight of about 50 kD (data not shown).

The wild-type and mutant human gamma-1 Fc regions were also expressed as LFA-3/Fc-fusion proteins, comprising human LFA-3 (Wallner et al., op. cit.), and the hinge-Fc region of the heavy chain constant regions of human gamma-1 (Ellison et al., op. cit.). As described above, the wild-type or mutant Fc-fusion expression vectors were stably transfected into NS0 cells for expression of LFA-3/Fc-fusion proteins. The expressed proteins were purified by protein A affinity chromatography.

Purified LFA-3/Fc-fusion proteins were characterized by SDS-PAGE. SDS-PAGE analysis under reducing conditions indicated that the purified Fc-fusion proteins consisted of a predominant species with a molecular weight of about 45 kD (data not shown).

Example 7

This example describes the competitive binding analysis of mutant IgG1 Fc-fusion proteins.

Cell Culture:

Mouse myeloma cell line NS0 was maintained in DMEM (BioWhittaker™) containing 10% FBS (HyClone®). NS0 transfectants expressing recombinant, GPI-linked human FcRn on the surface were maintained in 2× MPA selection medium.

Human FcRn Cell Line:

NS0 cells were stably transfected with pDL208. Approximately $1 \times 10^7$ cells were washed once and resuspended in 1 ml of plain DMEM (BioWhittaker™), transferred to a Gene Pulser™ Cuvette (Bio-Rad® Laboratories), and incubated on ice for 10 minutes. Forty µg of plasmid pDL208 was linearized with FspI and gently mixed with the cells on ice, then the cells were electroporated by pulsing twice using a Gene Pulser™ II (Bio-Rad® Laboratories) set at 1.5 kV, 3 µF, and returned to ice for 10 minutes. The cells were diluted in 20 ml of DMEM (BioWhittaker™), 10% FBS (HyClone®), and plated in two 96-well plates at 100 µl/well. The medium was replaced after 48 hours with MPA selection medium. Mycophenolic acid-resistant NS0 transfectants from wells apparently containing single colonies were expanded in MPA selection medium and screened after about 3 weeks by FACS™. Approximately $1.5 \times 10^5$ cells/test were incubated in 100 µl of FACS Staining Buffer (FSB) (PBS, 1% FBS, 0.1% $NaN_3$) containing 10 µg/ml of biotinylated mouse anti-human β2-microglobulin antibody (Chromaprobe, Inc., Aptos, Calif.) for 1 hour on ice. The cells were washed once with 4 ml of FSB, then incubated in 25 µl of FSB containing 20 µg/ml of streptavidin-FITC conjugate (Southern Biotechnology Associates, Inc., Birmingham, Ala.) for 30 minutes on ice in the dark. The cells were washed once with 4 ml of FSB, and resuspended in 1% formaldehyde. Samples were analyzed for antibody binding to human β2m using a FACScan™ flow cytometer (BD® Biosciences, San Jose, Calif.). Several clones with the highest apparent staining were subcloned using a FACStar cell sorter (BD® Biosciences), expanded in DMEM (BioWhittaker™), 10% FBS (HyClone®), 2 mM L-glutamine (Invitrogen™), and retested by FACS™ as described above. One subclone, designated NS0 HuFcRn (memb), clone 7-3, was used in subsequent binding assays.

Competitive Binding Assays:

A dilution series of each purified TNF-RII/Fc-fusion protein was competed against biotinylated TNF-RII/Fc-fusion protein for binding to human FcRn on cell line NS0 HuFcRn (memb), clone 7-3. Approximately $2 \times 10^5$ cells/test were washed once in FACS Binding Buffer (FBB) (PBS containing 0.5% BSA, 0.1% $NaN_3$), pH 8.0, and once in FBB, pH 6.0, then resuspended in 100 µl of pre-mixed biotinylated (Pierce Biotechnology, Rockford, Ill.) TNF-RII/Fc-fusion protein (8.3 µg/ml) and TNF-RII/Fc-fusion protein competitor (twofold serial dilutions from 208 µg/ml to 0.102 µg/ml) in FBB, pH 6.0. The cells were incubated with the Fc-fusion protein mixture for 1 hour on ice, washed twice in FBB, pH 6.0, and resuspended in 25 µl of streptavidin-RPE conjugate (BioSource International, Camarillo, Calif.) diluted to 2.5 µg/ml in FBB, pH 6.0. After incubation for 30 minutes on ice in the dark, the cells were washed twice in FBB, pH 6.0, and resuspended in 1% formaldehyde. Samples were analyzed for Fc-fusion protein binding to FcRn by FACS™ using a FACSCalibur™ flow cytometer (BD® Biosciences). Mean channel fluorescence (MCF) was plotted against competitor concentration, and IC50 values were calculated using GraphPad Prism® (GraphPad™ Software, Inc., San Diego, Calif.).

A dilution series of each purified IL-13/Fc-fusion protein was competed against human IgG (Sigma-Aldrich) that had been labeled with biotin (Pierce Biotechnology). Competitive binding assays were performed, as described above, using cell line NS0 HuFcRn (memb), clone 7-3. Cells were washed twice as described above and resuspended in 100 µl of pre-mixed biotinylated human IgG (8.3 µg/ml) and IL-13/Fc-fusion protein competitor (twofold serial dilutions from 208 µg/ml to 0.102 µg/ml or threefold serial dilutions from 219 µg/ml to 0.037 µg/ml) in FBB, pH 6.0, then processed as described above and analyzed by flow cytometry.

A dilution series of each purified LFA-3/Fc-fusion protein was competed against human IgG (Sigma-Aldrich) that had been labeled with biotin (Pierce Biotechnology). Competitive binding assays were performed, as described above, using cell line NS0 HuFcRn (memb), clone 7-3. Cells were washed twice as described above and resuspended in 100 μl of pre-mixed biotinylated human IgG (8.3 μg/ml) and LFA-3/Fc-fusion protein competitor (threefold serial dilutions from 219 μg/ml to 0.037 μg/ml) in FBB, pH 6.0, then processed as described above and analyzed by flow cytometry.

Results:

The relative binding of wild-type TNF-RII/Fc-fusion protein and its mutants to FcRn was determined using a transfected NS0 cell line stably expressing human FcRn on its surface. As described above, the purified Fc-fusion proteins were tested for FcRn binding in a competitive binding assay. Increasing concentrations of unlabeled competitor were incubated with cell line NS0 HuFcRn (memb), clone 7-3, in the presence of a sub-saturating concentration of labeled TNF-RII/Fc-fusion protein FBB, pH 6.0.

Plots of the MCF data versus competitor concentration exhibited the typical sigmoidal curve shape expected for assays of protein binding affinity. The double mutant (T250Q/M428L) exhibited slightly better binding to human FcRn than the single mutant (M428L), and was reproducibly ~2-fold better-binding to human FcRn than the wild-type TNF-RII/Fc-fusion protein.

Purified IL-13/Fc-fusion proteins were tested for FcRn binding in competitive binding assays. Increasing concentrations of unlabeled competitor were incubated with cell line NS0 HuFcRn (memb), clone 7-3, in the presence of a sub-saturating concentration of labeled human IgG (Sigma-Aldrich) in FBB, pH 6.0. As summarized in Table 2, the IC50 value for the wild-type IL-13/Fc-fusion protein was ~8 μg/ml, whereas the IC50 for the T250Q/M428L double mutant was ~0.5 μg/ml. The T250Q/M428L double mutant showed an approximate 15-fold increase in binding compared to the wild-type version of this IL-13/Fc-fusion protein.

TABLE 2

| Name[a] (IL-13/Fc-fusion) | n[b] | IC50 (μg/ml)[c] | Relative Binding[d] |
|---|---|---|---|
| Wild-type | 3 | 8.21 ± 2.34 | 1.0 |
| T250Q/M428L | 3 | 0.553 ± 0.226 | 15 |

[a]For the mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated human IgG (Sigma-Aldrich) in FBB, pH 6.0, as described in Example 7.
[d]Relative binding to human FcRn was calculated as the ratio of the IC50 value of the wild-type IL-13/Fc-fusion protein to that of the mutant.

For confirmation, IL-13/Fc-fusion proteins purified from stable transfections also were tested for FcRn binding in competitive binding assays as described above. As summarized in Table 3, the IC50 value for the wild-type IL-13/Fc-fusion protein was ~8 μg/ml, whereas the IC50 for the T250Q/M428L double mutant was ~0.6 μg/ml. The T250Q/M428L double mutant showed an approximate 14-fold increase in binding compared to the wild-type version of this IL-13/Fc-fusion protein.

TABLE 3

| Name[a] (IL-13/Fc-fusion) | n[b] | IC50 (μg/ml)[c] | Relative Binding[d] |
|---|---|---|---|
| Wild-type | 2 | 8.26 ± 6.29 | 1.0 |
| T250Q/M428L | 2 | 0.508 ± 0.481 | 14 |

[a]For the mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated human IgG (Sigma-Aldrich) in FBB, pH 6.0, as described in Example 7.
[d]Relative binding to human FcRn was calculated as the ratio of the IC50 value of the wild-type IL-13/Fc-fusion protein to that of the mutant.

LFA-3/Fc-fusion proteins purified from stable transfections were tested for FcRn binding in competitive binding assays. Increasing concentrations of unlabeled competitor were incubated with cell line NS0 HuFcRn (memb), clone 7-3, in the presence of a sub-saturating concentration of labeled human IgG (Sigma-Aldrich) in FBB, pH 6.0. Plots of the MCF data versus competitor concentration exhibited the typical sigmoidal curve shape expected for assays of protein binding affinity. As summarized in Table 4, the IC50 value for the wild-type LFA-3/Fc-fusion protein was ~3 μg/ml, whereas the IC50 for the T250Q/M428L double mutant was ~0.15 μg/ml. The T250Q/M428L double mutant showed an approximate 22-fold increase in binding compared to the wild-type version of this LFA-3/Fc-fusion protein.

TABLE 4

| Name[a] (LFA-3/Fc-fusion) | n[b] | IC50 (μg/ml)[c] | Relative Binding[d] |
|---|---|---|---|
| Wild-type | 3 | 3.31 ± 0.56 | 1.0 |
| T250Q/M428L | 3 | 0.148 ± 0.010 | 22 |

[a]For the mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated human IgG (Sigma-Aldrich) in FBB, pH 6.0, as described in Example 7.
[d]Relative binding to human FcRn was calculated as the ratio of the IC50 value of the wild-type LFA-3/Fc-fusion protein to that of the mutant.

Example 8

This example describes the pH-dependent binding analysis of mutant IgG1 Fc-fusion proteins.

pH-Dependent Binding and Release Assay:

IL-13 and LFA-3 wild-type and mutant Fc-fusion proteins, purified from stable transfections, were compared for binding to human FcRn and then released at various pH values in single-point binding and release assays using cell line NS0 HuFcRn (memb), clone 7-3. Approximately 2×10$^5$ cells/test were washed once in FBB, pH 8.0, and once in FBB, pH 6.0, then resuspended in 100 μl of purified Fc-fusion protein (5 μg/ml) in FBB, pH 6.0. The cells were incubated for 1 hour on ice, washed twice in FBB, pH 6.0, 6.5, 7.0, 7.5, or 8.0, and resuspended in 25 μl of goat F(ab')$_2$ anti-human IgG FITC-conjugated antibody (Jackson ImmunoResearch Laboratories, West Grove, Pa.) diluted to 0.34 μg/ml in FBB of the appropriate pH. After incubation for 30 minutes on ice in the dark, the cells were washed twice in FBB of the appropriate pH, and resuspended in 1% formaldehyde. Samples were analyzed for Fc-fusion protein binding to FcRn by FACS™ using a FACSCalibur™ flow cytometer (BD® Biosciences).

Results:

The binding of IgG to FcRn is known to be pH-dependent: IgG binds strongly to FcRn at pH 6.0 but weakly at pH 8.0. In order to engineer mutant Fc-fusion proteins with longer serum half-lives, it is desirable to increase binding to FcRn at pH 6.0, while retaining pH-dependent release from FcRn at pH 8.0. To confirm that binding was pH-dependent, the Fc-fusion proteins were tested for binding to a transfected NS0 cell line stably expressing human FcRn and then released at pH values ranging from pH 6.0 to pH 8.0. As described above, the cells were incubated with a sub-saturating concentration of antibody in FBB, pH 6.0, washed with FBB, pH 6.0, 6.5, 7.0, 7.5, or 8.0, and binding was analyzed by FACS™.

The modified IL-13/Fc-fusion protein with the T250Q/M428L mutation exhibited pH-dependent binding to human FcRn. The binding (as measured by MCF) was strongest at pH 6.0, and progressively diminished as the pH values increased to pH 6.5, 7.0, 7.5 and 8.0. The binding of the unmodified, wild-type IL-13/Fc fusion (as measured by MCF) exhibited a very similar pH dependence.

The modified LFA-3/Fc-fusion protein with the T250Q/M428L mutation also exhibited pH-dependent binding to human FcRn. Like the modified IL-13/Fc-fusion protein, binding (as measured by MCF) was strongest at pH 6.0, and progressively diminished as the pH values increased to pH 6.5, 7.0, 7.5 and 8.0. Once again, the measured pH dependence of the T250Q/M428L mutant mirrored that observed for the unmodified, wild-type LFA-3/Fc-fusion protein.

Example 9

This example describes the analysis of CD2 binding for LFA-3/Fc-fusion proteins.

Binding Assay on Jurkat Cells:

Purified LFA-3/Fc-fusion proteins were tested for binding to CD2 on Jurkat cells (American Type Culture Collection, Manassas, Va.). Approximately 2×10$^5$ cells/test were washed twice in FBB, pH 7.5, then resuspended in 100 µl of LFA-3/Fc-fusion protein at 125 µg/ml in FBB, pH 7.5. The cells were incubated for 1 hour on ice, washed twice in FBB, pH 7.5, and resuspended in 25 µl of goat F(ab')$_2$ anti-human IgG FITC-conjugated antibody (Jackson ImmunoResearch Laboratories) diluted to 0.34 µg/ml in FBB, pH 7.5. After incubation for 30 minutes on ice in the dark, the cells were washed twice in FBB, pH 7.5, and resuspended in 1% formaldehyde. Samples were analyzed for binding to CD2 by FACS™ using a FACSCalibur™ flow cytometer (BD® Biosciences).

Results:

The modified LFA-3/Fc-fusion protein having the T250Q/M428L mutation exhibited a CD2 binding profile similar to the wild-type LFA-3/Fc-fusion protein. These results indicate that the T250Q/M428L mutation does not affect CD2 binding.

Example 10

This example describes in vitro characterization and in vivo serum half-life assays of human IgG Fc-fusion proteins.

The affinity of human IgG Fc-fusion protein mutants to FcRn may be measured in vitro by various methods such as surface plasmon resonance (SPR) using soluble FcRn conjugated to a suitable biosensor chip, or by performing a competitive binding experiment using FcRn expressed on the surface of transfected cells. The FcRn used in the in vitro affinity experiments may be of murine, rhesus, cynomolgus, baboon, or human origin.

The serum half-life (e.g. the in vivo elimination half-life) of human IgG Fc-fusion protein mutants with the desired properties may be measured in vivo by injecting suitable experimental animals (e.g., mice, including strains deficient in endogenous FcRn and transgenic for human FcRn (Roopenian et al., J. Immunol. 170:3528–3533 (2003)) or monkeys) or humans with a dose of IgG Fc-fusion protein in the range 0.1–10 mg of protein per kg of body weight, then withdrawing serum samples at various time intervals spanning the expected serum half-life of the IgG Fc-fusion protein, and assaying the samples for the presence of intact IgG Fc-fusion protein by a suitable technique such as ELISA. This data may then be analyzed to determine whether the modified IgG Fc-fusion protein exhibits an increased in vivo elimination half-life.

It is understood that the examples described above in no way serve to limit the true scope of this invention, but rather are presented for illustrative purposes. All publications, patents and patent applications cited in this specification are herein incorporated by reference as if each individual publication or patent application were specifically and individually indicated to be incorporated by reference.

We claim:

1. A modified Fc-fusion protein comprising amino acid residues 250 and 428 that differ from the residues present in an unmodified Fc-fusion protein by amino acid residue 250 being glutamic acid or glutamine and amino acid residue 428 being leucine or phenylalanine, and wherein amino acid residues are numbered by the EU numbering system, and the Fc region of the modified Fc-fusion protein is of IgG isotype.

2. The modified Fc-fusion protein according to claim 1, wherein the unmodified Fc-fusion protein comprises an Fc region of a human antibody.

3. The modified Fc-fusion protein according to claim 2, wherein the human antibody is selected from the group consisting of human IgG1, IgG2, IgG2M3, IgG3 and IgG4 molecule.

4. The modified Fc-fusion protein according to claim 1 wherein
   (a) amino acid residue 250 is glutamie acid and amino acid residue 428 is phenylalanine; or
   (b) amino acid residue 250 is glutamine and amino acid residue 428 is phenylalanine; or
   (c) amino acid residue 250 is glutamine and amino acid residue 428 is leucine.

5. The modified Fc-fusion protein according to claim 1 wherein the modified Fc-fusion protein has a higher affinity for FcRn at pH 6.0 than at pH 8.0.

6. An Fc-fusion protein comprising an Fc region of a naturally occurring class IgG antibody, provided that amino acid residues 250 and 428 differ from the residues present in an unmodified Fc-fusion protein by amino acid residue 250 being glutamic acid or glutamine and amino acid residue 428 being leucine or phenylalanine, and wherein amino acid residues are numbered by the EU numbering system.

7. The Fc-fusion protein according to claim 6, wherein said naturally occurring antibody is a human antibody.

8. The Fc-fusion protein according to claim 6, wherein said naturally occurring class IgG antibody is selected from the group consisting of a human IgG1, IgG2, IgG3 and IgG4 molecule.

9. The Fc-fusion protein according to claim 6, wherein amino acid residue 250 from the Fc region of the antibody is glutamine.

10. The Fc-fusion protein according to claim 6, wherein amino acid residue 428 from the Fc region of the antibody is leucine.

11. A modified Fc-fusion protein of claim 1 with an in vivo mean elimination half-life at least about 1.3-fold longer than that of the unmodified Fc-fusion protein.

12. The modified Fc-fusion protein of claim 4 with an in vivo mean elimination half-life at least about 1.3-fold longer than that of the unmodified Fc-fusion protein.

13. A method for altering FcRn binding affinity and/or serum half-life of an Fc-fusion protein, said method comprising selecting amino acid residues 250 and 428 present in the Fc region of an Fc-fusion protein, and substituting amino acid residue 250 with glutamic acid or glutamine and amino acid residue 428 with leucine or phenylalanine, and wherein the amino acid residues are numbered by the EU numbering system and the Fc region is of IgG isotype.

14. A method of producing a modified Fc-fusion protein with an altered binding affinity for FcRn and/or an altered serum half-life as compared with the unmodified Fc-fusion protein, said method comprising:
   (a) preparing an expression vector comprising a suitable promoter operably linked to DNA encoding at least an Fc region of an IgG heavy chain comprising amino acid residues 250 and 428 that are substituted with glutamic acid or glutamine at amino acid residue 250 and leucine or phenylalanine at amino acid residue 428, wherein the amino acid residues are numbered by the EU numbering system;
   (b) transforming host cells with said vector; and
   (c) culturing said transformed host cells to produce said modified Fc-fusion protein.

15. The method according to claim 14, wherein:
   (a) amino acid residue 250 is substituted with glutamic acid and amino acid residue 428 is substituted with phenylalanine; or
   (b) amino acid residue 250 is substituted with glutamine and amino acid residue 428 is substituted with phenylalanine; or
   (c) amino acid residue 250 is substituted with glutamine and amino acid residue 428 is substituted with leucine.

* * * * *

UNITED STATES PATENT AND TRADEMARK OFFICE
CERTIFICATE OF CORRECTION

PATENT NO. : 7,217,798 B2  Page 1 of 4
APPLICATION NO. : 10/966673
DATED : May 15, 2007
INVENTOR(S) : Paul R. Hinton and Naoya Tsurushita It is certified that error appears in the above-identified patent and that said Letters Patent is hereby corrected as shown below:

In the Sequence Listing:

SEQ ID NO 58, Column 141, <212> type, delete "PRT" and insert --DNA--
SEQ ID NO 58, Column 141, delete
"Ala Ala Cys Cys Cys Ala Ala Gly Gly Ala Cys Cys Ala Ala Cys Thr
 1           5           10          15
   Cys Ala Thr Gly Ala Thr Cys Thr Cys Cys Cys Gly
        20          25"
and insert
--aacccaagga ccaactcatg atctcccg                         28--

SEQ ID NO 59, Column 141, <212> type, delete "PRT" and insert --DNA--
SEQ ID NO 59, Column 141, delete
"Gly Gly Ala Gly Ala Thr Cys Ala Thr Gly Ala Gly Thr Thr Gly Gly
 1           5           10          15
   Thr Cys Cys Thr Thr Gly Gly Gly Thr Thr Thr Thr Gly
        20          25"
and insert
--ggagatcatg agttggtcct tgggttttg                        29--

SEQ ID NO 60, Column 141, <212> type, delete "PRT" and insert --DNA--
SEQ ID NO 60, Column 141, delete
"Gly Thr Cys Cys Ala Cys Ala Cys Gly Ala Thr Cys Cys Cys Ala Ala
 1           5           10          15
   Cys Ala Cys Ala Cys Gly Cys Ala Gly
        20          25"
and insert
--gtccacacga tcccaacaca cgcag                            25--

Signed and Sealed this
Seventh Day of June, 2011

David J. Kappos
*Director of the United States Patent and Trademark Office*

CERTIFICATE OF CORRECTION (continued)
U.S. Pat. No. 7,217,798 B2

SEQ ID NO 61, Column 141, <212> type, delete "PRT" and insert --DNA--
SEQ ID NO 61, Column 141, delete
"Thr Ala Thr Ala Gly Ala Gly Ala Thr Cys Thr Gly Gly Cys Gly Cys
1               5                   10                  15
 Ala Cys Thr Ala Ala Ala Ala Ala Cys
            20                  25"
and insert
--tatagagatc tggcgcacta aaaac                        25--

SEQ ID NO 62, Column 141, <212> type, delete "PRT" and insert --DNA--
SEQ ID NO 62, Column 143, delete
"Cys Thr Cys Ala Thr Gly Cys Thr Cys Cys Gly Thr Gly Thr Thr Gly
1               5                   10                  15
   Cys Ala Thr Gly Ala Gly Gly Cys Thr Cys Thr Gly Cys
            20                  25"
and insert
--ctcatgctcc gtgttgcatg aggctctgc                    29--

SEQ ID NO 63, Column 143, <212> type, delete "PRT" and insert --DNA--
SEQ ID NO 63, Column 143, delete
"Ala Gly Ala Gly Cys Cys Thr Cys Ala Thr Gly Cys Ala Ala Cys Ala
1               5                   10                  15
   Cys Gly Gly Ala Gly Cys Ala Thr Gly Ala Gly
            20                  25"
and insert
--agagcctcat gcaacacgga gcatgag                      27--

SEQ ID NO 64, Column 143, <212> type, delete "PRT" and insert --DNA--
SEQ ID NO 64, Column 143, delete
"Cys Cys Thr Cys Ala Gly Cys Thr Cys Gly Gly Ala Cys Ala Cys Cys
1               5                   10                  15
     Thr Thr Cys Thr Cys
              20"
and insert
--cctcagctcg gacaccttct c                            21--

SEQ ID NO 65, Column 143, <212> type, delete "PRT" and insert --DNA--
SEQ ID NO 65, Column 143, delete
"Gly Cys Cys Thr Cys Cys Cys Thr Cys Ala Thr Gly Cys Cys Ala Cys
1               5                   10                  15
     Thr Cys Ala"
and insert
--gcctccctca tgccactca                               19--

CERTIFICATE OF CORRECTION (continued)

SEQ ID NO 69, Column 151, <212> type, delete "PRT" and insert --DNA--
SEQ ID NO 69, Column 151, delete
"Ala Cys Thr Ala Cys Cys Gly Gly Thr Gly Gly Gly Gly Gly Gly Gly
    1            5            10           15
    Cys Thr Gly Cys Ala Gly Ala Cys Ala Ala Ala Ala Cys Thr Cys Ala
            20            25           30
    Cys Ala Cys Ala
        35"
and insert
--actaccggtg gggggggctgc agacaaaact cacaca         36--

SEQ ID NO 70, Column 151, <212> type, delete "PRT" and insert --DNA--
SEQ ID NO 70, Column 151, delete
"Gly Cys Ala Cys Cys Cys Ala Gly Cys Gly Cys Thr Gly Cys Cys Cys
    1            5            10           15
    Thr"
and insert
--gcacccagcg ctgccct         17--

SEQ ID NO 73, Column 155, <212> type, delete "PRT" and insert --DNA--
SEQ ID NO 73, Columns 155-57, delete
"Cys Cys Ala Thr Ala Gly Ala Ala Gly Ala Cys Ala Cys Cys Gly Gly
    1            5            10           15
    Gly Ala Cys Cys
        20"
and insert
--ccatagaaga caccgggacc         20--

SEQ ID NO 74, Column 157, <212> type, delete "PRT" and insert --DNA--
SEQ ID NO 74, Column 157, delete
"Gly Ala Gly Thr Thr Thr Thr Gly Thr Cys Gly Ala Cys Ala Thr Ala
    1            5            10           15
    Ala Ala Gly Ala Ala Ala Gly Ala Ala Cys
        20            25"
and insert
--gagttttgtc gacataaaga aagaac         26--

CERTIFICATE OF CORRECTION (continued)

U.S. Pat. No. 7,217,798 B2

SEQ ID NO 75, Column 157, <212> type, delete "PRT" and insert --DNA--

SEQ ID NO 75, Column 157, delete

"Thr Cys Thr Thr Thr Cys Thr Thr Thr Ala Thr Gly Thr Cys Gly Ala
  1        5         10         15

Cys Ala Ala Ala Ala Cys Thr Cys Ala Cys Ala Cys Ala Thr Gly Cys
          20         25         30

Cys"

and insert

--tctttcttta tgtcgacaaa actcacacat gcc                      33--

SEQUENCE LISTING

```
<160> NUMBER OF SEQ ID NOS: 77

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Ala Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Cys Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 330
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

-continued

```
            115                 120                 125
Lys Pro Lys Asp Asp Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 330
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Glu Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

-continued

```
Tyr Val Asp Gly Val Glu Val His Asn Ala Lys Thr Lys Pro Arg Glu
            165                 170                 175
Glu Gln Tyr Asn Ser Thr Tyr Arg Val Val Ser Val Leu Thr Val Leu
        180                 185                 190
His Gln Asp Trp Leu Asn Gly Lys Glu Tyr Lys Cys Lys Val Ser Asn
    195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
            245                 250                 255
Pro Ser Asp Ile Ala Val Glu Trp Glu Ser Asn Gly Gln Pro Glu Asn
        260                 265                 270
Asn Tyr Lys Thr Thr Pro Pro Val Leu Asp Ser Asp Gly Ser Phe Phe
    275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330

<210> SEQ ID NO 5
<211> LENGTH: 330
<212> TYPE: PRT
<213> ORGANISM: Homo sapiens

<400> SEQUENCE: 5

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
            85                  90                  95
Lys Val Glu Pro Lys Ser Cys Asp Lys Thr His Thr Cys Pro Pro Cys
        100                 105                 110
Pro Ala Pro Glu Leu Leu Gly Gly Pro Ser Val Phe Leu Phe Pro Pro
    115                 120                 125
Lys Pro Lys Asp Phe Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
            165                 170                 175
Glu Gln Tyr Asn Ser Thr Tyr Arg Val Val Ser Val Leu Thr Val Leu
        180                 185                 190
His Gln Asp Trp Leu Asn Gly Lys Glu Tyr Lys Cys Lys Val Ser Asn
    195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 330
<212> TYPE: PRT
<213> ORGANISM: HOMO SAPIENS

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Gly Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
                        245                 250                 255
Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 7
<211> LENGTH: 330
<212> TYPE: PRT
<213> ORGANISM: HOMO SAPIENS

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp His Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330

<210> SEQ ID NO 8
<211> LENGTH: 330
<212> TYPE: PRT
<213> ORGANISM: HOMO SAPIENS

<400> SEQUENCE: 8

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Ile Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330
```

<210> SEQ ID NO 9
<211> LENGTH: 330
<212> TYPE: PRT
<213> ORGANISM: HOMO SAPIENS

<400> SEQUENCE: 9

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Lys Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 10
<211> LENGTH: 330
<212> TYPE: PRT
<213> ORGANISM: HOMO SAPIENS

<400> SEQUENCE: 10

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Leu Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 11
<211> LENGTH: 330
<212> TYPE: PRT
<213> ORGANISM: HOMO SAPIENS

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

-continued

```
                35                  40                  45
Gly Val His Thr Phe Pro Ala Val Leu Gln Ser Ser Gly Leu Tyr Ser
         50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Met Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 12
<211> LENGTH: 330
<212> TYPE: PRT
<213> ORGANISM: HOMO SAPIENS

<400> SEQUENCE: 12

Ala Ser Thr Lys Gly Pro Ser Val Phe Pro Leu Ala Pro Ser Ser Lys
  1               5                  10                  15
Ser Thr Ser Gly Gly Thr Ala Ala Leu Gly Cys Leu Val Lys Asp Tyr
             20                  25                  30
Phe Pro Glu Pro Val Thr Val Ser Trp Asn Ser Gly Ala Leu Thr Ser
         35                  40                  45
Gly Val His Thr Phe Pro Ala Val Leu Gln Ser Ser Gly Leu Tyr Ser
     50                  55                  60
Leu Ser Ser Val Val Thr Val Pro Ser Ser Ser Leu Gly Thr Gln Thr
 65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Asn Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 330
<212> TYPE: PRT
<213> ORGANISM: HOMO SAPIENS

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Pro Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 14
<211> LENGTH: 330
<212> TYPE: PRT
<213> ORGANISM: HOMO SAPIENS

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Gln Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                    165                 170                 175
Glu Gln Tyr Asn Ser Thr Tyr Arg Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 330
<212> TYPE: PRT
<213> ORGANISM: HOMO SAPIENS

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Arg Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 16
<211> LENGTH: 330
<212> TYPE: PRT
<213> ORGANISM: HOMO SAPIENS

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Ser Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 17
<211> LENGTH: 330
<212> TYPE: PRT
<213> ORGANISM: HOMO SAPIENS

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Val Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn

```
                290                 295                 300
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 18
<211> LENGTH: 330
<212> TYPE: PRT
<213> ORGANISM: HOMO SAPIENS

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Trp Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 19
<211> LENGTH: 330
<212> TYPE: PRT
<213> ORGANISM: HOMO SAPIENS

<400> SEQUENCE: 19

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Tyr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 20
<211> LENGTH: 330
<212> TYPE: PRT
<213> ORGANISM: HOMO SAPIENS

<400> SEQUENCE: 20

-continued

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Ala Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 21
<211> LENGTH: 330
<212> TYPE: PRT
<213> ORGANISM: HOMO SAPIENS

<400> SEQUENCE: 21

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Cys Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 22
<211> LENGTH: 330
<212> TYPE: PRT
<213> ORGANISM: HOMO SAPIENS

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
```

```
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
            130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Asp Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 23
<211> LENGTH: 330
<212> TYPE: PRT
<213> ORGANISM: HOMO SAPIENS

<400> SEQUENCE: 23

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
            115                 120                 125
```

```
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Glu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 24
<211> LENGTH: 330
<212> TYPE: PRT
<213> ORGANISM: HOMO SAPIENS

<400> SEQUENCE: 24

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Phe Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 25
<211> LENGTH: 330
<212> TYPE: PRT
<213> ORGANISM: HOMO SAPIENS

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Gly Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
                210                 215                 220
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 330
<212> TYPE: PRT
<213> ORGANISM: HOMO SAPIENS

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp His Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 330
<212> TYPE: PRT
<213> ORGANISM: HOMO SAPIENS

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Ile Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 28
<211> LENGTH: 330
<212> TYPE: PRT
<213> ORGANISM: HOMO SAPIENS

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Lys Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 29
<211> LENGTH: 330
<212> TYPE: PRT
<213> ORGANISM: HOMO SAPIENS

<400> SEQUENCE: 29

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Met Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 30
<211> LENGTH: 330
<212> TYPE: PRT
<213> ORGANISM: HOMO SAPIENS

<400> SEQUENCE: 30

```
Ala Ser Thr Lys Gly Pro Ser Val Phe Pro Leu Ala Pro Ser Ser Lys
```

```
             1               5                  10                 15
Ser Thr Ser Gly Gly Thr Ala Ala Leu Gly Cys Leu Val Lys Asp Tyr
                    20                  25                  30

Phe Pro Glu Pro Val Thr Val Ser Trp Asn Ser Gly Ala Leu Thr Ser
                    35                  40                  45

Gly Val His Thr Phe Pro Ala Val Leu Gln Ser Ser Gly Leu Tyr Ser
                    50                  55                  60

Leu Ser Ser Val Val Thr Val Pro Ser Ser Ser Leu Gly Thr Gln Thr
 65                      70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                    100                 105                 110

Pro Ala Pro Glu Leu Leu Gly Gly Pro Ser Val Phe Leu Phe Pro Pro
                    115                 120                 125

Lys Pro Lys Asp Thr Leu Met Ile Ser Arg Thr Pro Glu Val Thr Cys
                    130                 135                 140

Val Val Val Asp Val Ser His Glu Asp Pro Glu Val Lys Phe Asn Trp
145                     150                 155                 160

Tyr Val Asp Gly Val Glu Val His Asn Ala Lys Thr Lys Pro Arg Glu
                    165                 170                 175

Glu Gln Tyr Asn Ser Thr Tyr Arg Val Val Ser Val Leu Thr Val Leu
                    180                 185                 190

His Gln Asp Trp Asn Asn Gly Lys Glu Tyr Lys Cys Lys Val Ser Asn
                    195                 200                 205

Lys Ala Leu Pro Ala Pro Ile Glu Lys Thr Ile Ser Lys Ala Lys Gly
                    210                 215                 220

Gln Pro Arg Glu Pro Gln Val Tyr Thr Leu Pro Pro Ser Arg Asp Glu
225                     230                 235                 240

Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
                    275                 280                 285

Leu Tyr Ser Lys Leu Thr Val Asp Lys Ser Arg Trp Gln Gln Gly Asn
                    290                 295                 300

Val Phe Ser Cys Ser Val Met His Glu Ala Leu His Asn His Tyr Thr
305                     310                 315                 320

Gln Lys Ser Leu Ser Leu Ser Pro Gly Lys
                    325                 330

<210> SEQ ID NO 31
<211> LENGTH: 330
<212> TYPE: PRT
<213> ORGANISM: HOMO SAPIENS

<400> SEQUENCE: 31

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                    20                  25                  30

Phe Pro Glu Pro Val Thr Val Ser Trp Asn Ser Gly Ala Leu Thr Ser
                    35                  40                  45
```

```
Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Pro Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 32
<211> LENGTH: 330
<212> TYPE: PRT
<213> ORGANISM: HOMO SAPIENS

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Gln Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
        210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 33
<211> LENGTH: 330
<212> TYPE: PRT
<213> ORGANISM: HOMO SAPIENS

<400> SEQUENCE: 33

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
```

```
                130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Arg Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 34
<211> LENGTH: 330
<212> TYPE: PRT
<213> ORGANISM: HOMO SAPIENS

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Ser Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 35
<211> LENGTH: 330
<212> TYPE: PRT
<213> ORGANISM: HOMO SAPIENS

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Thr Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

-continued

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

<210> SEQ ID NO 36
<211> LENGTH: 330
<212> TYPE: PRT
<213> ORGANISM: HOMO SAPIENS

<400> SEQUENCE: 36

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Val Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
```

```
                        260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 37
<211> LENGTH: 330
<212> TYPE: PRT
<213> ORGANISM: HOMO SAPIENS

<400> SEQUENCE: 37

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Trp Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
```

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 38
<211> LENGTH: 330
<212> TYPE: PRT
<213> ORGANISM: HOMO SAPIENS

<400> SEQUENCE: 38

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Tyr Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 39

```
<211> LENGTH: 330
<212> TYPE: PRT
<213> ORGANISM: HOMO SAPIENS

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Ala His Glu Ala Leu His Asn His Tyr Thr
305                 310                 315                 320

Gln Lys Ser Leu Ser Leu Ser Pro Gly Lys
                325                 330

<210> SEQ ID NO 40
<211> LENGTH: 330
<212> TYPE: PRT
<213> ORGANISM: HOMO SAPIENS

<400> SEQUENCE: 40

Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                    165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Cys His Glu Ala Leu His Asn His Tyr Thr
305                 310                 315                 320

Gln Lys Ser Leu Ser Leu Ser Pro Gly Lys
                325                 330

<210> SEQ ID NO 41
<211> LENGTH: 330
<212> TYPE: PRT
<213> ORGANISM: HOMO SAPIENS

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser

-continued

```
                    50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Asp His Glu Ala Leu His Asn His Tyr Thr
305                 310                 315                 320

Gln Lys Ser Leu Ser Leu Ser Pro Gly Lys
                325                 330
```

<210> SEQ ID NO 42
<211> LENGTH: 330
<212> TYPE: PRT
<213> ORGANISM: HOMO SAPIENS

<400> SEQUENCE: 42

```
Ala Ser Thr Lys Gly Pro Ser Val Phe Pro Leu Ala Pro Ser Ser Lys
  1                   5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
              35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                     85                  90                  95
```

-continued

```
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Glu His Glu Ala Leu His Asn His Tyr Thr
305                 310                 315                 320
Gln Lys Ser Leu Ser Leu Ser Pro Gly Lys
                325                 330
```

<210> SEQ ID NO 43
<211> LENGTH: 330
<212> TYPE: PRT
<213> ORGANISM: HOMO SAPIENS

<400> SEQUENCE: 43

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Phe His Glu Ala Leu His Asn His Tyr Thr
305                 310                 315                 320

Gln Lys Ser Leu Ser Leu Ser Pro Gly Lys
                325                 330

<210> SEQ ID NO 44
<211> LENGTH: 330
<212> TYPE: PRT
<213> ORGANISM: HOMO SAPIENS

<400> SEQUENCE: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
```

-continued

```
                180                 185                 190
His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Gly His Glu Ala Leu His Asn His Tyr Thr
305                 310                 315                 320

Gln Lys Ser Leu Ser Leu Ser Pro Gly Lys
                325                 330

<210> SEQ ID NO 45
<211> LENGTH: 330
<212> TYPE: PRT
<213> ORGANISM: HOMO SAPIENS

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val His His Glu Ala Leu His Asn His Tyr Thr
305                 310                 315                 320

Gln Lys Ser Leu Ser Leu Ser Pro Gly Lys
                325                 330

<210> SEQ ID NO 46
<211> LENGTH: 330
<212> TYPE: PRT
<213> ORGANISM: HOMO SAPIENS

<400> SEQUENCE: 46

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270
```

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Ile His Glu Ala Leu His Asn His Tyr Thr
305                 310                 315                 320

Gln Lys Ser Leu Ser Leu Ser Pro Gly Lys
            325                 330

<210> SEQ ID NO 47
<211> LENGTH: 330
<212> TYPE: PRT
<213> ORGANISM: HOMO SAPIENS

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Lys His Glu Ala Leu His Asn His Tyr Thr

Gln Lys Ser Leu Ser Leu Ser Pro Gly Lys
            325                 330

<210> SEQ ID NO 48
<211> LENGTH: 330
<212> TYPE: PRT
<213> ORGANISM: HOMO SAPIENS

<400> SEQUENCE: 48

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Asn His Tyr Thr
305                 310                 315                 320

Gln Lys Ser Leu Ser Leu Ser Pro Gly Lys
            325                 330

<210> SEQ ID NO 49
<211> LENGTH: 330

```
<212> TYPE: PRT
<213> ORGANISM: HOMO SAPIENS

<400> SEQUENCE: 49

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Asn His Glu Ala Leu His Asn His Tyr Thr
305                 310                 315                 320

Gln Lys Ser Leu Ser Leu Ser Pro Gly Lys
                325                 330

<210> SEQ ID NO 50
<211> LENGTH: 330
<212> TYPE: PRT
<213> ORGANISM: HOMO SAPIENS

<400> SEQUENCE: 50

Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Pro His Glu Ala Leu His Asn His Tyr Thr
305                 310                 315                 320

Gln Lys Ser Leu Ser Leu Ser Pro Gly Lys
                325                 330

<210> SEQ ID NO 51
<211> LENGTH: 330
<212> TYPE: PRT
<213> ORGANISM: HOMO SAPIENS

<400> SEQUENCE: 51

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60
```

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Gln His Glu Ala Leu His Asn His Tyr Thr
305                 310                 315                 320

Gln Lys Ser Leu Ser Leu Ser Pro Gly Lys
                325                 330

<210> SEQ ID NO 52
<211> LENGTH: 330
<212> TYPE: PRT
<213> ORGANISM: HOMO SAPIENS

<400> SEQUENCE: 52

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110
```

-continued

```
                100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Arg His Glu Ala Leu His Asn His Tyr Thr
305                 310                 315                 320
Gln Lys Ser Leu Ser Leu Ser Pro Gly Lys
                325                 330

<210> SEQ ID NO 53
<211> LENGTH: 330
<212> TYPE: PRT
<213> ORGANISM: HOMO SAPIENS

<400> SEQUENCE: 53

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Ser His Glu Ala Leu His Asn His Tyr Thr
305                 310                 315                 320

Gln Lys Ser Leu Ser Leu Ser Pro Gly Lys
                325                 330

<210> SEQ ID NO 54
<211> LENGTH: 330
<212> TYPE: PRT
<213> ORGANISM: HOMO SAPIENS

<400> SEQUENCE: 54

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Thr His Glu Ala Leu His Asn His Tyr Thr
305                 310                 315                 320

Gln Lys Ser Leu Ser Leu Ser Pro Gly Lys
                325                 330

<210> SEQ ID NO 55
<211> LENGTH: 330
<212> TYPE: PRT
<213> ORGANISM: HOMO SAPIENS

<400> SEQUENCE: 55

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
```

```
                225                 230                 235                 240
Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Val Phe Ser Cys Ser Val Val His Glu Ala Leu His Asn His Tyr Thr
305                 310                 315                 320

Gln Lys Ser Leu Ser Leu Ser Pro Gly Lys
                325                 330

<210> SEQ ID NO 56
<211> LENGTH: 330
<212> TYPE: PRT
<213> ORGANISM: HOMO SAPIENS

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270
```

-continued

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Trp His Glu Ala Leu His Asn His Tyr Thr
305                 310                 315                 320

Gln Lys Ser Leu Ser Leu Ser Pro Gly Lys
            325                 330

<210> SEQ ID NO 57
<211> LENGTH: 330
<212> TYPE: PRT
<213> ORGANISM: HOMO SAPIENS

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Tyr His Glu Ala Leu His Asn His Tyr Thr
305                 310                 315                 320
```

Gln Lys Ser Leu Ser Leu Ser Pro Gly Lys
            325                 330

<210> SEQ ID NO 58
<211> LENGTH: 28
<212> TYPE: PRT
<213> ORGANISM: ARTIFICIAL
<220> FEATURE:
<223> OTHER INFORMATION: primer

SEQUENCE: 58

Ala Ala Cys Cys Cys Ala Ala Gly Gly Ala Cys Ala Ala Cys Thr
1               5                   10                  15

Cys Ala Thr Gly Ala Thr Cys Thr Cys Cys Gly
            20                  25

<210> SEQ ID NO 59
<211> LENGTH: 29
<212> TYPE: PRT
<213> ORGANISM: ARTIFICIAL
<220> FEATURE:
<223> OTHER INFORMATION: primer

SEQUENCE: 59

Gly Gly Ala Gly Ala Thr Cys Ala Thr Gly Ala Gly Thr Thr Gly Gly
1               5                   10                  15

Thr Cys Cys Thr Thr Gly Gly Gly Thr Thr Thr Thr Gly
            20                  25

<210> SEQ ID NO 60
<211> LENGTH: 25
<212> TYPE: PRT
<213> ORGANISM: ARTIFICIAL
<220> FEATURE:
<223> OTHER INFORMATION: primer

SEQUENCE: 60

Gly Thr Cys Cys Ala Cys Ala Cys Gly Ala Thr Cys Cys Ala Ala
1               5                   10                  15

Cys Ala Cys Ala Cys Gly Cys Ala Gly
            20                  25

<210> SEQ ID NO 61
<211> LENGTH: 25
<212> TYPE: PRT
<213> ORGANISM: ARTIFICIAL
<220> FEATURE:
<223> OTHER INFORMATION: primer

<400> SEQUENCE: 61

Thr Ala Thr Ala Gly Ala Gly Ala Thr Cys Thr Gly Gly Cys Gly Cys
1               5                   10                  15

Ala Cys Thr Ala Ala Ala Ala Ala Cys
            20                  25

<210> SEQ ID NO 62
<211> LENGTH: 29
<212> TYPE: PRT
<213> ORGANISM: ARTIFICIAL
<220> FEATURE:
<223> OTHER INFORMATION: primer

<400> SEQUENCE: 62

-continued

Cys Thr Cys Ala Thr Gly Cys Thr Cys Gly Thr Gly Thr Thr Gly
1               5                   10                  15

Cys Ala Thr Gly Ala Gly Gly Cys Thr Cys Thr Gly Cys
            20                  25

<210> SEQ ID NO 63
<211> LENGTH: 27
<212> TYPE: PRT
<213> ORGANISM: ARTIFICIAL
<220> FEATURE:
<223> OTHER INFORMATION: primer

<400> SEQUENCE: 63

Ala Gly Ala Gly Cys Cys Thr Cys Ala Thr Gly Cys Ala Ala Cys Ala
1               5                   10                  15

Cys Gly Gly Ala Gly Cys Ala Thr Gly Ala Gly
            20                  25

<210> SEQ ID NO 64
<211> LENGTH: 21
<212> TYPE: PRT
<213> ORGANISM: ARTIFICIAL
<220> FEATURE:
<223> OTHER INFORMATION: primer

<400> SEQUENCE: 64

Cys Cys Thr Cys Ala Gly Cys Thr Gly Gly Ala Cys Ala Cys Cys
1               5                   10                  15

Thr Thr Cys Thr Cys
            20

<210> SEQ ID NO 65
<211> LENGTH: 19
<212> TYPE: PRT
<213> ORGANISM: ARTIFICIAL
<220> FEATURE:
<223> OTHER INFORMATION: primer

<400> SEQUENCE: 65

Gly Cys Cys Thr Cys Cys Cys Thr Cys Ala Thr Gly Cys Cys Ala Cys
1               5                   10                  15

Thr Cys Ala

<210> SEQ ID NO 66
<211> LENGTH: 471
<212> TYPE: PRT
<213> ORGANISM: ARTIFICIAL
<220> FEATURE:
<223> OTHER INFORMATION: fusion protein

<400> SEQUENCE: 66

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys

```
                    85                  90                  95
Thr Cys Arg Pro Gly Trp Tyr Cys Ala Leu Ser Lys Gln Glu Gly Cys
                100                 105                 110
Arg Leu Cys Ala Pro Leu Arg Lys Cys Arg Pro Gly Phe Gly Val Ala
            115                 120                 125
Arg Pro Gly Thr Glu Thr Ser Asp Val Val Cys Lys Pro Cys Ala Pro
        130                 135                 140
Gly Thr Phe Ser Asn Thr Thr Ser Ser Thr Asp Ile Cys Arg Pro His
145                 150                 155                 160
Gln Ile Cys Asn Val Val Ala Ile Pro Gly Asn Ala Ser Met Asp Ala
                165                 170                 175
Val Cys Thr Ser Thr Ser Pro Thr Arg Ser Met Ala Pro Gly Ala Val
                180                 185                 190
His Leu Pro Gln Pro Val Ser Thr Arg Ser Gln His Thr Gln Pro Thr
            195                 200                 205
Pro Glu Pro Ser Thr Ala Pro Ser Thr Ser Phe Leu Leu Pro Met Gly
        210                 215                 220
Pro Ser Pro Pro Ala Glu Gly Ser Thr Gly Asp Thr Gly Gly Gly Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
                260                 265                 270
Asp Thr Leu Met Ile Ser Arg Thr Pro Glu Val Thr Cys Val Val Val
            275                 280                 285
Asp Val Ser His Glu Asp Pro Glu Val Lys Phe Asn Trp Tyr Val Asp
        290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
        355                 360                 365
Glu Pro Gln Val Tyr Thr Leu Pro Pro Ser Arg Asp Glu Leu Thr Lys
        370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
            435                 440                 445
Cys Ser Val Met His Glu Ala Leu His Asn His Tyr Thr Gln Lys Ser
450                 455                 460
Leu Ser Leu Ser Pro Gly Lys
465                 470

<210> SEQ ID NO 67
<211> LENGTH: 471
<212> TYPE: PRT
<213> ORGANISM: ARTIFICIAL
```

-continued

```
<220> FEATURE:
<223> OTHER INFORMATION: fusion protein

<400> SEQUENCE: 67

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Thr Gly Gly Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400
```

-continued

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Leu His Glu Ala Leu His Asn His Tyr Thr Gln Lys Ser
    450                 455                 460

Leu Ser Leu Ser Pro Gly Lys
465                 470

<210> SEQ ID NO 68
<211> LENGTH: 471
<212> TYPE: PRT
<213> ORGANISM: ARTIFICIAL
<220> FEATURE:
<223> OTHER INFORMATION: fusion protein

<400> SEQUENCE: 68

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Thr Gly Gly Gly Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Gln Leu Met Ile Ser Arg Thr Pro Glu Val Thr Cys Val Val Val
        275                 280                 285

-continued

```
Asp Val Ser His Glu Asp Pro Glu Val Lys Phe Asn Trp Tyr Val Asp
    290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
        355                 360                 365
Glu Pro Gln Val Tyr Thr Leu Pro Pro Ser Arg Asp Glu Leu Thr Lys
    370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Leu His Glu Ala Leu His Asn His Tyr Thr Gln Lys Ser
    450                 455                 460
Leu Ser Leu Ser Pro Gly Lys
465                 470

<210> SEQ ID NO 69
<211> LENGTH: 36
<212> TYPE: PRT
<213> ORGANISM: ARTIFICIAL
<220> FEATURE:
<223> OTHER INFORMATION: primer

<400> SEQUENCE: 69

Ala Cys Thr Ala Cys Cys Gly Gly Thr Gly Gly Gly Gly Gly Gly Gly
1               5                   10                  15
Cys Thr Gly Cys Ala Gly Ala Cys Ala Ala Ala Cys Thr Cys Ala
            20                  25                  30
Cys Ala Cys Ala
        35

<210> SEQ ID NO 70
<211> LENGTH: 17
<212> TYPE: PRT
<213> ORGANISM: ARTIFICIAL
<220> FEATURE:
<223> OTHER INFORMATION: primer

<400> SEQUENCE: 70

Gly Cys Ala Cys Cys Ala Gly Cys Gly Cys Thr Gly Cys Cys
1               5                   10                  15
Thr

<210> SEQ ID NO 71
<211> LENGTH: 345
<212> TYPE: PRT
<213> ORGANISM: ARTIFICIAL
<220> FEATURE:
<223> OTHER INFORMATION: fusion protein
```

<400> SEQUENCE: 71

```
Gly Pro Val Pro Ser Thr Ala Leu Arg Glu Leu Ile Glu Glu Leu
 1               5                  10                  15
Val Asn Ile Thr Gln Asn Gln Lys Ala Pro Leu Cys Asn Gly Ser Met
             20                  25                  30
Val Trp Ser Ile Asn Leu Thr Ala Gly Met Tyr Cys Ala Ala Leu Glu
         35                  40                  45
Ser Leu Ile Asn Val Ser Gly Cys Ser Ala Ile Glu Lys Thr Gln Arg
     50                  55                  60
Met Leu Gly Gly Phe Cys Pro His Lys Val Ser Ala Gly Gln Phe Ser
 65                  70                  75                  80
Ser Leu His Val Arg Asp Thr Lys Ile Glu Val Ala Gln Phe Val Lys
                 85                  90                  95
Asp Leu Leu Leu His Leu Lys Lys Leu Phe Arg Glu Gly Arg Phe Asn
            100                 105                 110
Thr Gly Gly Gly Ala Ala Asp Lys Thr His Thr Cys Pro Pro Cys Pro
        115                 120                 125
Ala Pro Glu Leu Leu Gly Gly Pro Ser Val Phe Leu Phe Pro Pro Lys
130                 135                 140
Pro Lys Asp Thr Leu Met Ile Ser Arg Thr Pro Glu Val Thr Cys Val
145                 150                 155                 160
Val Val Asp Val Ser His Glu Asp Pro Glu Val Lys Phe Asn Trp Tyr
                165                 170                 175
Val Asp Gly Val Glu Val His Asn Ala Lys Thr Lys Pro Arg Glu Glu
            180                 185                 190
Gln Tyr Asn Ser Thr Tyr Arg Val Val Ser Val Leu Thr Val Leu His
        195                 200                 205
Gln Asp Trp Leu Asn Gly Lys Glu Tyr Lys Cys Lys Val Ser Asn Lys
210                 215                 220
Ala Leu Pro Ala Pro Ile Glu Lys Thr Ile Ser Lys Ala Lys Gly Gln
225                 230                 235                 240
Pro Arg Glu Pro Gln Val Tyr Thr Leu Pro Pro Ser Arg Asp Glu Leu
                245                 250                 255
Thr Lys Asn Gln Val Ser Leu Thr Cys Leu Val Lys Gly Phe Tyr Pro
            260                 265                 270
Ser Asp Ile Ala Val Glu Trp Glu Ser Asn Gly Gln Pro Glu Asn Asn
        275                 280                 285
Tyr Lys Thr Thr Pro Pro Val Leu Asp Ser Asp Gly Ser Phe Phe Leu
290                 295                 300
Tyr Ser Lys Leu Thr Val Asp Lys Ser Arg Trp Gln Gln Gly Asn Val
305                 310                 315                 320
Phe Ser Cys Ser Val Met His Glu Ala Leu His Asn His Tyr Thr Gln
                325                 330                 335
Lys Ser Leu Ser Leu Ser Pro Gly Lys
            340                 345
```

<210> SEQ ID NO 72
<211> LENGTH: 345
<212> TYPE: PRT
<213> ORGANISM: ARTIFICIAL
<220> FEATURE:
<223> OTHER INFORMATION: fusion protein

<400> SEQUENCE: 72

Gly Pro Val Pro Pro Ser Thr Ala Leu Arg Glu Leu Ile Glu Glu Leu

```
            1               5                   10                  15
        Val Asn Ile Thr Gln Asn Gln Lys Ala Pro Leu Cys Asn Gly Ser Met
                        20                  25                  30

Val Trp Ser Ile Asn Leu Thr Ala Gly Met Tyr Cys Ala Ala Leu Glu
                        35                  40                  45

Ser Leu Ile Asn Val Ser Gly Cys Ser Ala Ile Glu Lys Thr Gln Arg
                    50                  55                  60

Met Leu Gly Gly Phe Cys Pro His Lys Val Ser Ala Gly Gln Phe Ser
        65                  70                  75                  80

Ser Leu His Val Arg Asp Thr Lys Ile Glu Val Ala Gln Phe Val Lys
                        85                  90                  95

Asp Leu Leu His Leu Lys Lys Leu Phe Arg Glu Gly Arg Phe Asn
                        100                 105                 110

Thr Gly Gly Gly Ala Ala Asp Lys Thr His Thr Cys Pro Pro Cys Pro
                    115                 120                 125

Ala Pro Glu Leu Leu Gly Gly Pro Ser Val Phe Leu Phe Pro Pro Lys
                    130                 135                 140

Pro Lys Asp Gln Leu Met Ile Ser Arg Thr Pro Glu Val Thr Cys Val
        145                 150                 155                 160

Val Val Asp Val Ser His Glu Asp Pro Glu Val Lys Phe Asn Trp Tyr
                        165                 170                 175

Val Asp Gly Val Glu Val His Asn Ala Lys Thr Lys Pro Arg Glu Glu
                    180                 185                 190

Gln Tyr Asn Ser Thr Tyr Arg Val Val Ser Val Leu Thr Val Leu His
                    195                 200                 205

Gln Asp Trp Leu Asn Gly Lys Glu Tyr Lys Cys Lys Val Ser Asn Lys
        210                 215                 220

Ala Leu Pro Ala Pro Ile Glu Lys Thr Ile Ser Lys Ala Lys Gly Gln
        225                 230                 235                 240

Pro Arg Glu Pro Gln Val Tyr Thr Leu Pro Pro Ser Arg Asp Glu Leu
                        245                 250                 255

Thr Lys Asn Gln Val Ser Leu Thr Cys Leu Val Lys Gly Phe Tyr Pro
                        260                 265                 270

Ser Asp Ile Ala Val Glu Trp Glu Ser Asn Gly Gln Pro Glu Asn Asn
                    275                 280                 285

Tyr Lys Thr Thr Pro Pro Val Leu Asp Ser Asp Gly Ser Phe Phe Leu
                    290                 295                 300

Tyr Ser Lys Leu Thr Val Asp Lys Ser Arg Trp Gln Gln Gly Asn Val
        305                 310                 315                 320

Phe Ser Cys Ser Val Leu His Glu Ala Leu His Asn His Tyr Thr Gln
                        325                 330                 335

Lys Ser Leu Ser Leu Ser Pro Gly Lys
                        340                 345

<210> SEQ ID NO 73
<211> LENGTH: 20
<212> TYPE: PRT
<213> ORGANISM: ARTIFICIAL
<220> FEATURE:
<223> OTHER INFORMATION: primer

<400> SEQUENCE: 73

Cys Cys Ala Thr Ala Gly Ala Ala Gly Ala Cys Ala Cys Gly Gly
1               5                   10                  15

Gly Ala Cys Cys
```

-continued

<210> SEQ ID NO 74
<211> LENGTH: 26
<212> TYPE: PRT
<213> ORGANISM: ARTIFICIAL
<220> FEATURE:
<223> OTHER INFORMATION: primer

<400> SEQUENCE: 74

Gly Ala Gly Thr Thr Thr Gly Thr Cys Gly Ala Cys Ala Thr Ala
1               5                   10                  15

Ala Ala Gly Ala Ala Gly Ala Ala Cys
            20                  25

<210> SEQ ID NO 75
<211> LENGTH: 33
<212> TYPE: PRT
<213> ORGANISM: ARTIFICIAL
<220> FEATURE:
<223> OTHER INFORMATION: primer

<400> SEQUENCE: 75

Thr Cys Thr Thr Thr Cys Thr Thr Thr Ala Thr Gly Thr Cys Gly Ala
1               5                   10                  15

Cys Ala Ala Ala Cys Thr Cys Ala Cys Ala Cys Ala Thr Gly Cys
            20                  25                  30

Cys

<210> SEQ ID NO 76
<211> LENGTH: 319
<212> TYPE: PRT
<213> ORGANISM: ARTIFICIAL
<220> FEATURE:
<223> OTHER INFORMATION: fusion protein

<400> SEQUENCE: 76

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
            20                  25                  30

Asp Lys Val Ala Glu Leu Glu Asn Ser Glu Phe Arg Ala Phe Ser Ser
        35                  40                  45

Phe Lys Asn Arg Val Tyr Leu Asp Thr Val Ser Gly Ser Leu Thr Ile
    50                  55                  60

Tyr Asn Leu Thr Ser Ser Asp Glu Asp Glu Tyr Glu Met Glu Ser Pro
65                  70                  75                  80

Asn Ile Thr Asp Thr Met Lys Phe Phe Leu Tyr Val Asp Lys Thr His
                85                  90                  95

Thr Cys Pro Pro Cys Pro Ala Pro Glu Leu Leu Gly Gly Pro Ser Val
            100                 105                 110

Phe Leu Phe Pro Pro Lys Pro Lys Asp Thr Leu Met Ile Ser Arg Thr
        115                 120                 125

Pro Glu Val Thr Cys Val Val Val Asp Val Ser His Glu Asp Pro Glu
    130                 135                 140

Val Lys Phe Asn Trp Tyr Val Asp Gly Val Glu Val His Asn Ala Lys
145                 150                 155                 160

Thr Lys Pro Arg Glu Glu Gln Tyr Asn Ser Thr Tyr Arg Val Val Ser
                165                 170                 175

```
Val Leu Thr Val Leu His Gln Asp Trp Leu Asn Gly Lys Glu Tyr Lys
                180                 185                 190

Cys Lys Val Ser Asn Lys Ala Leu Pro Ala Pro Ile Glu Lys Thr Ile
            195                 200                 205

Ser Lys Ala Lys Gly Gln Pro Arg Glu Pro Gln Val Tyr Thr Leu Pro
        210                 215                 220

Pro Ser Arg Asp Glu Leu Thr Lys Asn Gln Val Ser Leu Thr Cys Leu
225                 230                 235                 240

Val Lys Gly Phe Tyr Pro Ser Asp Ile Ala Val Glu Trp Glu Ser Asn
                245                 250                 255

Gly Gln Pro Glu Asn Asn Tyr Lys Thr Thr Pro Pro Val Leu Asp Ser
            260                 265                 270

Asp Gly Ser Phe Phe Leu Tyr Ser Lys Leu Thr Val Asp Lys Ser Arg
        275                 280                 285

Trp Gln Gln Gly Asn Val Phe Ser Cys Ser Val Met His Glu Ala Leu
290                 295                 300

His Asn His Tyr Thr Gln Lys Ser Leu Ser Leu Ser Pro Gly Lys
305                 310                 315

<210> SEQ ID NO 77
<211> LENGTH: 319
<212> TYPE: PRT
<213> ORGANISM: ARTIFICIAL
<220> FEATURE:
<223> OTHER INFORMATION: fusion protein

<400> SEQUENCE: 77

Phe Ser Gln Gln Ile Tyr Gly Val Val Tyr Gly Asn Val Thr Phe His
1               5                   10                  15

Val Pro Ser Asn Val Pro Leu Lys Glu Val Leu Trp Lys Lys Gln Lys
                20                  25                  30

Asp Lys Val Ala Glu Leu Glu Asn Ser Glu Phe Arg Ala Phe Ser Ser
            35                  40                  45

Phe Lys Asn Arg Val Tyr Leu Asp Thr Val Ser Gly Ser Leu Thr Ile
        50                  55                  60

Tyr Asn Leu Thr Ser Ser Asp Glu Asp Glu Tyr Glu Met Glu Ser Pro
65                  70                  75                  80

Asn Ile Thr Asp Thr Met Lys Phe Phe Leu Tyr Val Asp Lys Thr His
                85                  90                  95

Thr Cys Pro Pro Cys Pro Ala Pro Glu Leu Leu Gly Gly Pro Ser Val
            100                 105                 110

Phe Leu Phe Pro Pro Lys Pro Lys Asp Gln Leu Met Ile Ser Arg Thr
        115                 120                 125

Pro Glu Val Thr Cys Val Val Val Asp Val Ser His Glu Asp Pro Glu
            130                 135                 140

Val Lys Phe Asn Trp Tyr Val Asp Gly Val Glu Val His Asn Ala Lys
145                 150                 155                 160

Thr Lys Pro Arg Glu Glu Gln Tyr Asn Ser Thr Tyr Arg Val Val Ser
                165                 170                 175

Val Leu Thr Val Leu His Gln Asp Trp Leu Asn Gly Lys Glu Tyr Lys
            180                 185                 190

Cys Lys Val Ser Asn Lys Ala Leu Pro Ala Pro Ile Glu Lys Thr Ile
        195                 200                 205

Ser Lys Ala Lys Gly Gln Pro Arg Glu Pro Gln Val Tyr Thr Leu Pro
        210                 215                 220
```

-continued

```
Pro Ser Arg Asp Glu Leu Thr Lys Asn Gln Val Ser Leu Thr Cys Leu
225             230                 235                 240

Val Lys Gly Phe Tyr Pro Ser Asp Ile Ala Val Glu Trp Glu Ser Asn
                245             250                 255

Gly Gln Pro Glu Asn Asn Tyr Lys Thr Thr Pro Pro Val Leu Asp Ser
            260             265                 270

Asp Gly Ser Phe Phe Leu Tyr Ser Lys Leu Thr Val Asp Lys Ser Arg
            275             280                 285

Trp Gln Gln Gly Asn Val Phe Ser Cys Ser Val Leu His Glu Ala Leu
    290             295             300

His Asn His Tyr Thr Gln Lys Ser Leu Ser Leu Ser Pro Gly Lys
305             310             315
```